(12) United States Patent
Sheng et al.

(10) Patent No.: US 10,759,798 B2
(45) Date of Patent: Sep. 1, 2020

(54) ABT-199 ADDITION SALT AND CRYSTAL FORM THEREOF, PREPARATION METHOD THEREOF, AND PHARMACEUTICAL COMPOSITION THEREOF

(71) Applicant: Hangzhou SoliPharma Co., Ltd, Hangzhou (CN)

(72) Inventors: Xiaohong Sheng, Hangzhou (CN); Xiaoxia Sheng, Hangzhou (CN); Jianfeng Zheng, Hangzhou (CN)

(73) Assignee: Hangzhou SoliPharma Co., Ltd., Hangzhou (CN)

( * ) Notice: Subject to any disclaimer, the term of this patent is extended or adjusted under 35 U.S.C. 154(b) by 0 days.

(21) Appl. No.: 16/333,243

(22) PCT Filed: Sep. 14, 2016

(86) PCT No.: PCT/CN2016/099139
§ 371 (c)(1),
(2) Date: Mar. 14, 2019

(87) PCT Pub. No.: WO2018/049634
PCT Pub. Date: Mar. 22, 2018

(65) Prior Publication Data
US 2019/0248788 A1    Aug. 15, 2019

(51) Int. Cl.
*A61K 31/437*    (2006.01)
*C07D 471/04*    (2006.01)
*A61P 35/00*    (2006.01)
*A61P 37/00*    (2006.01)
*A61P 35/02*    (2006.01)

(52) U.S. Cl.
CPC .......... *C07D 471/04* (2013.01); *A61K 31/437* (2013.01); *A61P 35/00* (2018.01); *A61P 37/00* (2018.01); *A61P 35/02* (2018.01); *C07B 2200/13* (2013.01)

(58) Field of Classification Search
CPC .......................... A61K 31/437; C07D 471/04
USPC ...................... 514/253.04; 544/362
See application file for complete search history.

(56) References Cited

PUBLICATIONS

Shundong Cang, et al., ABT-199 (venetoclax) and BCL-2 inhibitors in clinical development, Journal of Hematology & Oncology (2015) 8:129.

*Primary Examiner* — Jeffrey H Murray
(74) *Attorney, Agent, or Firm* — Duane Morris LLP; Thomas J. Kowalski; Deborah L. Lu

(57) ABSTRACT

Crystalline forms, preparation methods and pharmaceutical compositions of ABT-199 monohydrochloride and ABT-199 dihydrochloride are disclosed. Compared with known ABT-199, they have one or more improved properties. They can be used to prepare drugs for the treatment and/or prevention of one or more diseases associated with overexpression of an anti-apoptotic BCL-2 family protein.

21 Claims, 12 Drawing Sheets

ABT-199 ADDITION SALT AND CRYSTAL FORM THEREOF, PREPARATION METHOD THEREOF, AND PHARMACEUTICAL COMPOSITION THEREOF

FIELD OF THE INVENTION

The present invention relates to the technical field of crystallization in pharmaceutical chemistry. Specifically, the present invention relates to crystalline forms of ABT-199 hydrochloride and preparation methods and uses thereof as well as pharmaceutical compositions comprising the crystalline forms.

BACKGROUND

ABT-199 is a novel drug developed by Abbott for the treatment of chronic lymphocytic leukemia. It is a B-cell lymphoma factor-2 (BCL-2) inhibitor.

ABT-199, also known as GDC-0199 or GDC-199, has a chemical name of 4-(4-{[2-(4-chlorophenyl)-4,4-dimethyl-cyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy) benzamide, and is commonly referred to as Venetoclax. The molecular formula is $C_{45}H_{50}ClN_7O_7S$ and the molecular weight is 868.44. The formula of ABT-199 is as follows:

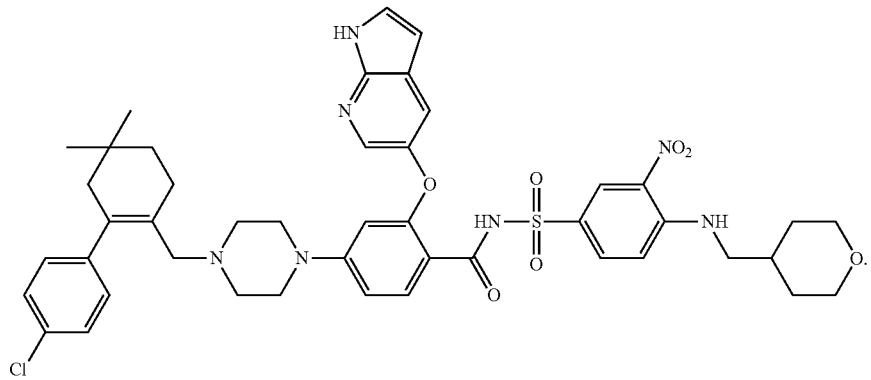 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

Chinese patent application CN103328474A describes a preparation method of ABT-199, various crystalline forms of free ABT-199, an ABT-199 monohydrochloride crystalline form (referred to as ABT-199 hydrochloride Form I in the present invention for differentiation purpose), an ABT-199 monohydrochloride hydrate (referred to as ABT-199 hydrochloride Form II in the present invention for differentiation purpose), and an ABT-199 sulfate and their PXRD characterization. It also describes their pharmaceutical compositions.

ABT-199 hydrochloride Form I disclosed in CN103328474A has poor stability, and is easily converted to ABT-199 hydrochloride Form II when exposed to air. The inventors of the present invention discovered that ABT-199 hydrochloride Form II disadvantageously has low solubility in water and poor stability at high temperature.

In view of the disadvantages in the prior art, it is necessary to find new solid forms of ABT-199 hydrochloride with more advantageous properties in this field.

SUMMARY OF THE INVENTION

In view of the disadvantages in the prior art, the objective of the present invention is to provide crystalline forms of ABT-199 hydrochloride and their preparation methods and uses, as well as the pharmaceutical compositions of ABT-199 hydrochloride forms. Compared to the known ABT-199 hydrochloride Form I and Form II, the crystalline forms of the present invention have one or more improved properties, particularly good solubility and stability.

Compared to the known ABT-199 monohydrochloride solid forms, the salts, crystalline forms or amorphous form of ABT-199 in the present invention have/has one or more advantageous properties. Specific improvements are, for example, higher solubility, higher dissolution rate, better stability, better flowability, and advantageous processing and handling characteristics. Particularly the novel solid forms of the present invention have higher solubility and better stability.

According to an objective of the present invention, the present invention provides ABT-199 monohydrochloride Form A (referred to as "Form A", in the present invention).

Form A is an ABT-199 monohydrochloride solvate formed with ethanol, and its structure is shown in the following formula (I):

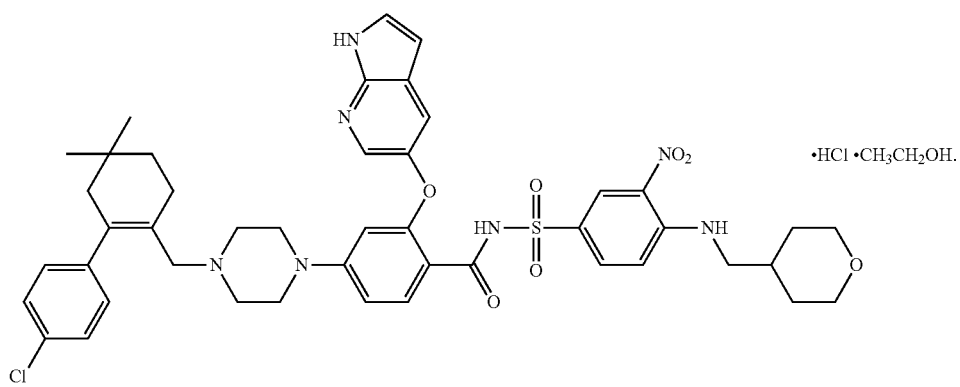

The Fourier transform infrared spectrum of Form A has characteristic peaks at wave numbers of 3384, 2971, 2861, 2524, 2362, 1700, 1595, 1315, 1270, 1119, 946, 818 and 710 $cm^1$.

According to an objective of the present invention, the present invention provides a preparation method of Form A, which comprises the steps of forming a suspension by placing the ABT-199 monohydrochloride solid in ethanol or in a mixed solvent of ethanol and another organic solvent, wherein the another solvent is water, alkane (including chloroalkane), $C_4$ to $C_5$ ester, $C_4$ to $C_6$ ether (including cyclic ether), acetonitrile, tetrahydrofuran or a mixture thereof; stirring the suspension for crystallization, separating and drying the precipitated crystals to obtain Form A.

Using Cu-Kα radiation, the X-ray powder diffraction pattern of Form A, expressed as 2θ angles, has the following characteristic peaks: 4.5±0.2°, 8.3±0.2°, 12.1±0.2°, 17.2±0.2°, 18.0±0.2° and 19.0±0.2°.

Preferably, the X-ray powder diffraction pattern of Form A, expressed as 2θ angles, has the following characteristic peaks: 4.5±0.2°, 8.3±0.2°, 9.4±0.2°, 12.1±0.2°, 17.2±0.2°, 18.0±0.2°, 19.0±0.2°, 19.5±0.2°, 20.8±0.2°, 23.0±0.2°, 24.7±0.2° and 27.0±0.2°.

More preferably, the X-ray powder diffraction pattern of Form A, expressed as 2θ angles, has the following characteristic peaks with their relative intensities:

| Diffraction angel 2θ | Relative intensity % |
|---|---|
| 4.5 ± 0.2° | 38.8 |
| 8.3 ± 0.2° | 45.3 |
| 9.4 ± 0.2° | 28.8 |
| 9.8 ± 0.2° | 17.4 |
| 12.1 ± 0.2° | 66.1 |
| 14.5 ± 0.2° | 19.2 |
| 17.2 ± 0.2° | 36.0 |
| 18.0 ± 0.2° | 100.0 |
| 19.0 ± 0.2° | 43.3 |
| 19.5 ± 0.2° | 24.7 |
| 20.8 ± 0.2° | 32.0 |
| 23.0 ± 0.2° | 41.4 |
| 23.5 ± 0.2° | 13.7 |
| 24.7 ± 0.2° | 22.3 |
| 26.2 ± 0.2° | 13.3 |
| 27.0 ± 0.2° | 29.5. |

Non-restrictively, in one specific embodiment of the present invention, the X-ray powder diffraction pattern of Form A is shown in FIG. 2.

Preferably, the another solvent is water, n-heptane, methyl tert-butyl ether, tetrahydrofuran or a mixture thereof.

Preferably, the operation temperature of the preparation method is from 10° C. to 60° C.; more preferably, room temperature; the stirring time is from 1 day to 7 days, more preferably, 3 days to 7 days.

Preferably, the drying temperature is from 10° C. to 60° C.; more preferably, 10° C. to 40° C.

Preferably, the drying time is from 10 hours to 48 hours; more preferably, 10 hours to 24 hours.

Preferably, the weight to volume ratio of ABT-199 monohydrochloride to the solvent is 10 mg/mL to 100 mg/mL, more preferably, 20 mg/mL to 50 mg/mL.

Form A has the following beneficial effects:

Form A of the present invention has a higher solubility in water at 25° C. than the known ABT-199 hydrochloride Form II. It indicates that Form A of the present invention has better solubility, and hence better bioavailability.

Form A of the present invention remains its appearance, XRPD and melting point unchanged even after being placed at room temperature and 10%-90% RH for 4 months. It indicates that Form A of the present invention has good storage stability, avoiding or reducing the occurrence of quality, safety and stability related problems, such as uneven active ingredient distribution and impurity mixing in, during drug manufacturing and/or storage of the pharmaceutically active ingredient itself and the formulations containing ABT-199 monohydrochloride, and also avoiding the use of special and expensive packaging.

According to an objective of the present invention, the present invention provides ABT-199 monohydrochloride Form B (referred to as "Form B" in the present invention).

Form B is an anhydrate of ABT-199 monohydrochloride, and its structure is shown in the following structure (II):

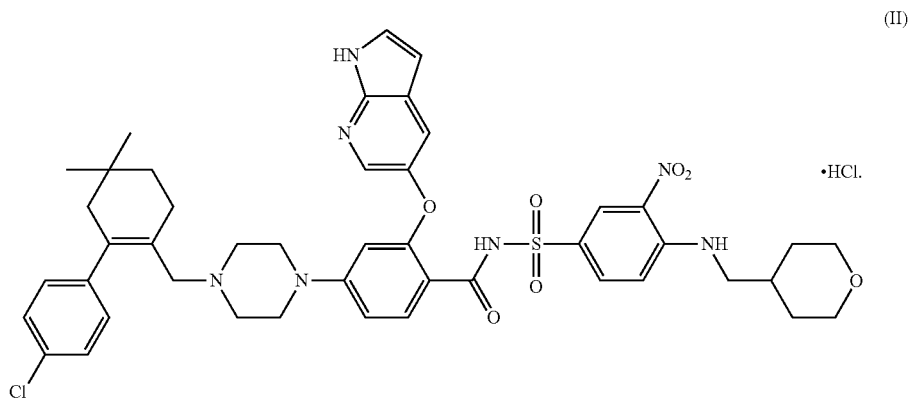 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1 ; "·HCl."]

(II)

Using Cu-Kα radiation, the X-ray powder diffraction pattern of Form B, expressed as 2θ angles, has the following characteristic peaks: 4.6±0.2°, 9.9±0.2°, 12.2±0.2°, 13.3±0.2°, 18.0±0.2° and 20.8±0.2°.

Preferably, the X-ray powder diffraction pattern of Form B, expressed as 2θ angles, has the following characteristic peaks: 4.6±0.2°, 7.2±0.2°, 9.1±0.2°, 9.9±0.2°, 12.2±0.2°, 13.3±0.2°, 18.0±0.2°, 18.8±0.2°, 19.1±0.2°, 20.8±0.2°, 22.0±0.2° and 27.0±0.2°.

More preferably, the X-ray powder diffraction pattern of Form B, expressed as 2θ angles, has the following characteristic peaks with their relative intensities:

| Diffraction angel 2θ | Relative intensity % |
|---|---|
| 4.6 ± 0.2° | 23.6 |
| 7.2 ± 0.2° | 20.1 |
| 9.1 ± 0.2° | 20.5 |
| 9.9 ± 0.2° | 31.1 |
| 11.7 ± 0.2° | 15.3 |
| 12.2 ± 0.2° | 25.1 |
| 13.3 ± 0.2° | 100.0 |
| 14.4 ± 0.2° | 21.9 |
| 16.8 ± 0.2° | 17.1 |
| 18.0 ± 0.2° | 29.0 |
| 18.8 ± 0.2° | 36.4 |
| 19.1 ± 0.2° | 37.3 |
| 20.8 ± 0.2° | 32.9 |
| 21.6 ± 0.2° | 17.7 |
| 22.0 ± 0.2° | 33.4 |
| 24.2 ± 0.2° | 23.3 |
| 27.0 ± 0.2° | 35.9 |

Non-restrictively, in one specific embodiment of the present invention, the X-ray powder diffraction pattern of Form B is shown in FIG. 5.

The Fourier transform infrared spectrum of Form B has characteristic peaks at wave numbers of 1669, 1573, 1431, 1367, 1229, 1205, 1143, 985, 866 and 811 cm$^{-1}$.

Preferably, Form B has the following single crystal structure information:

| Crystal form | the ABT-199 monohydrochloride Form B |
|---|---|
| Crystal system | Triclinic system |
| Space groups | P$_T$ |
| a (Å) | 12.5124 |
| b (Å) | 13.1206 |

| Crystal form | the ABT-199 monohydrochloride Form B |
|---|---|
| Crystal system | Triclinic system |
| Space groups | P$_T$ |
| c (Å) | 15.3840 |
| α (°) | 93.159 |
| β (°) | 96.314 |
| γ (°) | 113.909 |
| Z | 2. |

According to an objective of the present invention, the present invention provides a preparation method of Form B, which is either of the two following methods.

Method 1 comprises the steps of heating Form A or ABT-199 hydrochloride Form II from room temperature to 130° C. at a heating rate of 5 to 20° C./min, holding the sample at that temperature for 5 to 35 minutes until complete desolvation, and then cooling the sample to room temperature at a cooling rate of 5 to 20° C./min to obtain Form B.

The ABT-199 hydrochloride Form II has an X-ray powder diffraction pattern as shown in FIG. 1.

Preferably, the time of holding the sample at that temperature is 20 to 35 minutes, more preferably 20 to 30 minutes.

Preferably, the heating rate is 5 to 10° C./min.

Preferably, the cooling rate is 10 to 20° C./min.

Method 2 comprises the steps of keeping Form A or ABT-199 hydrochloride Form II at a temperature of 130 to 150° C. for a period of 20 to 40 minutes until the solvent is completely removed, and then keeping the resultant at room temperature to obtain Form B.

The ABT-199 hydrochloride Form II has an X-ray powder diffraction pattern as shown in FIG. 1.

Preferably, the temperature is 140 to 150° C.

Preferably, the time period of placing the sample at said temperature is 20 to 30 minutes.

Form B has the following beneficial effects:

The crystalline form of the known ABT-199 monohydrochloride Form II changes after being placed at 130° C. for 1 day, but the crystalline form of Form B does not change. It indicates that Form B of the present invention is more stable than the known ABT-199 monohydrochloride Form II.

The appearance, XRPD pattern and melting point of Form B of the present invention remains unchanged after being placed at room temperature and 10%-90% RH for 4 months. It indicates that Form B of the present invention has good storage stability, avoiding or reducing the occurrence of quality, safety and stability problems, such as uneven active ingredient distribution and impurity mixing in, during drug manufacturing and/or storage of the pharmaceutically active ingredient itself and the formulations containing ABT-199 monohydrochloride, and avoiding the use of special and expensive packaging.

According to an objective of the present invention, the present invention provides the ABT-199 monohydrochloride Form C (referred to as "Form C" in the present invention).

Form C is a ABT-199 monohydrochloride dihydrate, and its structure is shown in the following formula (III):

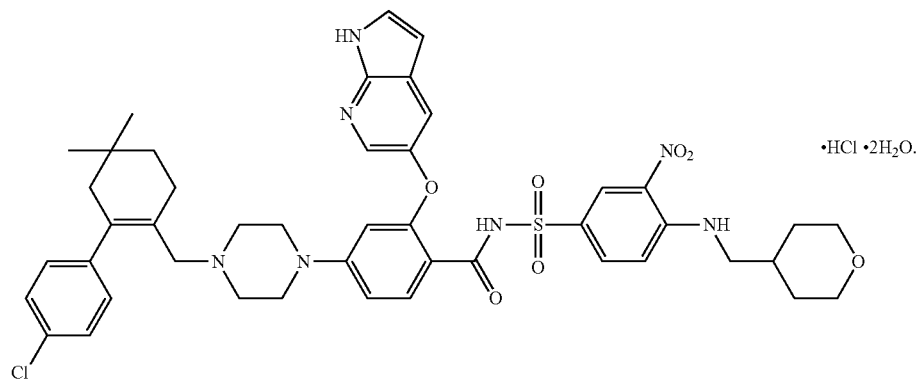

(III)

Using Cu-Kα radiation, the X-ray powder diffraction pattern of Form C, expressed as 2θ angles, has the following characteristic peaks: 4.6±0.2°, 8.3±0.2°, 11.9±0.2°, 17.2±0.2° and 17.8±0.2°.

Preferably, the X-ray powder diffraction pattern of Form C, expressed as 2θ angles, has the following characteristic peaks: 4.6±0.2°, 8.3±0.2°, 11.9±0.2°, 17.2±0.2°, 17.8±0.2°, 18.5±0.2°, 19.3±0.2°, 21.2±0.2°, 23.6±0.2° and 27.0±0.2°.

More preferably, the X-ray powder diffraction pattern of Form C, expressed as 2θ angles, has the following characteristic peaks with their relative intensities:

| Diffraction angel 2θ | Relative intensity % |
|---|---|
| 4.6 ± 0.2° | 56.6 |
| 8.3 ± 0.2° | 59.4 |
| 9.8 ± 0.2° | 19.1 |
| 11.9 ± 0.2° | 72.3 |
| 12.4 ± 0.2° | 25.0 |
| 15.3 ± 0.2° | 20.7 |
| 17.2 ± 0.2° | 58.2 |
| 17.8 ± 0.2° | 100.0 |
| 18.5 ± 0.2° | 35.5 |
| 19.3 ± 0.2° | 35.5 |
| 21.2 ± 0.2° | 39.3 |
| 22.3 ± 0.2° | 39.3 |
| 23.1 ± 0.2° | 17.0 |
| 23.6 ± 0.2° | 41.6 |
| 24.6 ± 0.2° | 22.5 |
| 27.0 ± 0.2° | 51.4 |

Non-restrictively, in one specific embodiment of the present invention, the X-ray powder diffraction pattern of Form C is shown in FIG. 7.

The Fourier transform infrared spectrum of Form C has characteristic peaks at wave numbers of 1669, 1605, 1522, 1418, 1367, 1346, 1250, 1173, 904 and 842 cm$^{-1}$.

According to an objective of the present invention, the present invention provides a preparation method of Form C, which comprises the steps of forming a suspension of ABT-199 monohydrochloride solid in dichloromethane, methanol, water-saturated ester/alkane, $C_3$ to $C_4$ ketone or a mixture thereof, stirring the suspension for crystallization, separating and drying the precipitated crystals to obtain Form C.

Preferably, the solvent is dichloromethane, methanol, water-saturated ethyl acetate, water-saturated n-heptane, methyl ethyl ketone or a mixture thereof.

Preferably, the preparation method has an operating temperature at 10 to 60° C., and more preferably at room temperature.

Preferably, the stirring time is from 1 to 7 days, more preferably from 3 to 7 days.

Preferably, the drying temperature is from 10 to 60° C., more preferably from 10 to 40° C.

Preferably, the drying time is from 10 to 48 hours, more preferably from 10 to 24 hours.

Preferably, the weight to volume ratio of ABT-199 monohydrochloride to solvent is 10 mg/mL to 100 mg/mL, more preferably, 20 mg/mL to 50 mg/mL.

Form C has the following beneficial effects:

By a comparative slurry stability competition experiment in solvents, it is known that the known ABT-199 monohydrochloride Form II is not able to maintain its original crystalline form and converted to Form C of the present invention, while Form C of the present invention remains unchanged under the same experimental conditions.

The appearance, XRPD pattern and melting point of Form C of the present invention remains unchanged after being placed at room temperature and 10%-90% RH for 4 months. It indicates that Form C of the present invention has good storage stability, avoiding or reducing the occurrence of quality, safety and stability problems, such as uneven active ingredient distribution and impurity mixing in, during drug manufacturing and/or storage of the pharmaceutically active ingredient itself and the formulations containing ABT-199 monohydrochloride, and avoiding the use of special and expensive packaging.

According to an objective of the present invention, the present invention provides ABT-199 dihydrochloride Form 1 (referred to as "Form 1" in the present invention), and its structure is shown in the following formula (IV):

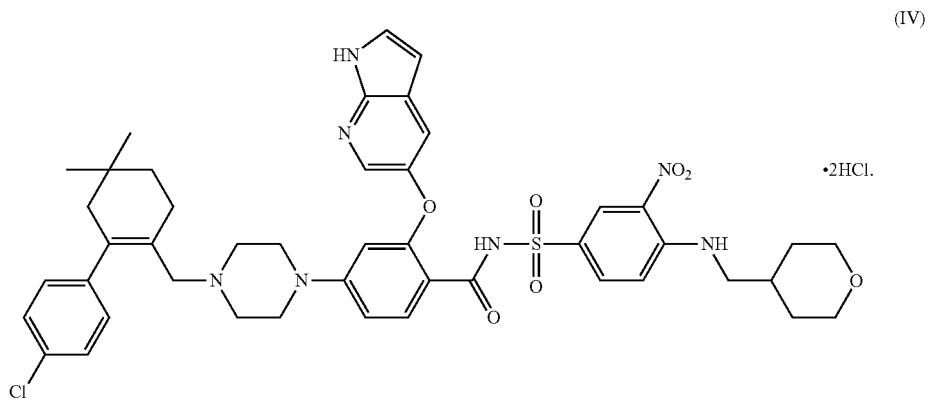 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

Form 1 is an anhydrous ABT-199 dihydrochloride.

Using Cu-Kα radiation, the X-ray powder diffraction pattern of Form 1, expressed as 2θ angles, has the following characteristic peaks: 4.5±0.2°, 9.9±0.2°, 12.4±0.2°, 16.5±0.2°, 19.0±0.2° and 20.7±0.2°.

Preferably, the X-ray powder diffraction pattern of Form 1, expressed as 2θ angles, has the following characteristic peaks: 4.5±0.2°, 9.9±0.2°, 12.4±0.2°, 15.5±0.2°, 16.5±0.2°, 16.7±0.2°, 17.2±0.2°, 19.0±0.2°, 19.6±0.2°, 20.7±0.2°, 22.9±0.2° and 25.2±0.2°.

More preferably, the X-ray powder diffraction pattern of Form 1, expressed as 2θ angles, has the following characteristic peaks with their relative intensities:

| Diffraction angel 2θ | Relative intensity % |
|---|---|
| 4.5 ± 0.2° | 100.0 |
| 9.9 ± 0.2° | 62.5 |
| 12.4 ± 0.2° | 20.8 |
| 13.2 ± 0.2° | 10.4 |
| 15.5 ± 0.2° | 19.0 |
| 16.5 ± 0.2° | 58.3 |
| 16.7 ± 0.2° | 25.5 |
| 17.2 ± 0.2° | 19.7 |
| 19.0 ± 0.2° | 26.2 |
| 19.6 ± 0.2° | 22.5 |
| 20.7 ± 0.2° | 57.1 |
| 22.9 ± 0.2° | 25.0 |
| 23.5 ± 0.2° | 14.4 |
| 25.2 ± 0.2° | 26.6 |
| 28.2 ± 0.2° | 12.9. |

Non-restrictively, in one specific embodiment of the present invention, the X-ray powder diffraction pattern of Form I is shown in FIG. 10.

The Fourier transform infrared spectrum of Form 1 has characteristic peaks at wave numbers of 1687, 1618, 1569, 1447, 1351, 1312, 1275, 1238, 1172, 1091, 831, 790 and 659 $cm^{-1}$.

According to an objective of the present invention, the present invention provides a preparation method of Form 1, which comprises the steps of mixing and stirring free ABT-199 with hydrochloric acid solution at a molar ratio of 1:2 to 1:2.5 in a solvent which is $C_1$ to $C_4$ alcohol, $C_3$ to $C_4$ ketone, acetonitrile or a mixture thereof, separating the resultant solid, and obtaining Form 1.

Preferably, the solvent is isopropanol, acetone, acetonitrile or a mixture thereof.

Preferably, the preparation method has an operating temperature of 10 to 50° C., more preferably room temperature.

Preferably, the stirring time is from 1 to 7 days, more preferably from 3 to 7 days.

Preferably, the drying temperature is from 10 to 60° C., more preferably from 10 to 40° C.

Preferably, the drying time is from 10 to 48 hours, more preferably from 10 to 24 hours.

Preferably, the weight to volume ratio of ABT-199 free base to solvent is 40 mg/mL to 100 mg/mL, more preferably, 40 mg/mL to 80 mg/mL.

The starting material ABT-199 can be prepared by the method described in the Examples of the patent application CN103328474A for synthesis of compound 1, which is incorporated into this application by reference in its entirety. It is also commercially available and can be amorphous or crystalline.

Form 1 has the following beneficial effects:

The solubility of Form 1 of the present invention in water at 25° C. is higher than that of ABT-199 hydrochloride Form II, indicating that Form 1 of the present invention has better solubility and hence better bioavailability.

The appearance, XRPD pattern and melting point of Form 1 of the present invention remains unchanged after being placed at room temperature and 10%-90% RH for 4 months. It indicates that Form 1 of the present invention has good storage stability, avoiding or reducing the occurrence of quality, safety and stability problems, such as uneven active ingredient distribution and impurity mixing in, during drug manufacturing and/or storage of the pharmaceutically active ingredient itself and the formulations containing ABT-199 dihydrochloride, and avoiding the use of special and expensive packaging.

The present inventors have also developed Form D, Form E, Form F, Form G, Form H, Form I, Form J, Form K, Form L, Form M and Form N of ABT-199 monohydrochloric and their preparation methods.

Compared with the known ABT-199 monohydrochloride solid forms, Form D, Form E, Form F, Form G, Form H, Form I, Form J, Form K, Form L, Form M and Form N of ABT-199 monohydrochloride have one or more improved properties, such as higher crystallinity, better solubility, higher dissolution rate, better crystal morphology, better thermal stability and storage stability, lower moisture absorption, better flowability and/or favorable processing and processing characteristics.

ABT-199 monohydrochloride Form D, with Cu-Kα radiation, has an X-ray powder diffraction pattern, expressed as 2θ angles, with the following characteristic peaks: 5.8±0.2°, 7.3±0.2°, 11.4±0.2°, 11.8±0.2°, 16.0±0.2°, 17.4±0.2°, 17.8±0.2°, 18.0±0.2°, 19.6±0.2°, 20.1±0.2°, 21.7±0.2° and 24.8±0.2°.

The invention also provides the preparation method of ABT-199 monohydrochloride Form D, which comprises the steps of forming a suspension of ABT-199 monohydrochloride solid in a solvent, stirring the mixture for crystallization at a certain temperature, separating and drying the precipitated crystals, and obtaining the ABT-199 monohydrochloride Form D. Preferably, the solvent is a mixed solvent of 1,4-dioxane and water, and the temperature is 10 to 60° C.

The ABT-199 monohydrochloride Form E, with Cu-Kα radiation, has an X-ray powder diffraction pattern, expressed as 2θ angles, with the following characteristic peaks: 4.6±0.2°, 8.3±0.2°, 12.1±0.2°, 17.3±0.2°, 17.9±0.2°, 18.2±0.2°, 18.9±0.2°, 19.5±0.2°, 20.8±0.2°, 22.9±0.2°, 23.5±0.2° and 24.6±0.2°.

The invention also provides the preparation method of ABT-199 monohydrochloride Form E, which comprises the steps of forming a suspension of ABT-199 monohydrochloride solid in toluene or a mixed solvent of toluene and another organic solvent, stirring the mixture for crystallization at a certain temperature, separating and drying the precipitated crystals, and obtaining ABT-199 monohydrochloride Form E. Preferably, the another organic solvent is alkane, $C_4$ to $C_5$ ester or a mixture thereof, and the temperature is 40 to 60° C.

ABT-199 monohydrochloride Form F, with Cu-Kα radiation, has an X-ray powder diffraction pattern of Form F, expressed as 2θ angles, with the following characteristic peaks: 4.6±0.2°, 8.4±0.2°, 12.0±0.2°, 13.1±0.2°, 14.7±0.2°, 17.8±0.2°, 19.2±0.2°, 20.9±0.2°, 23.1±0.2°, 24.7±0.2°, 26.3±0.2° and 27.1±0.2°.

The invention also provides the preparation method of ABT-199 monohydrochloride Form F, which comprises the steps of forming a suspension of ABT-199 monohydrochloride solid in chloroform or a mixed solvent of chloroform and another organic solvent, stirring the mixture for crystallization at a certain temperature, separating and drying the precipitated crystals, and obtaining ABT-199 monohydrochloride Form F. Preferably, the another organic solvent is alcohol, alkane (including chlorinated alkane), $C_4$ to $C_5$ ester or a mixture thereof, and the temperature is 40 to 60° C.

ABT-199 monohydrochloride Form G, with Cu-Kα radiation, has an X-ray powder diffraction pattern of Form G, expressed as 2θ angles, with the following characteristic peaks: 4.6±0.2°, 8.2±0.2°, 9.5±0.2°, 12.1±0.2°, 17.1±0.2°, 18.0±0.2°, 18.8±0.2°, 19.5±0.2°, 20.7±0.2°, 23.0±0.2°, 24.7±0.2° and 26.5±0.2°.

The invention also provides the preparation method of the ABT-199 monohydrochloride Form G, which comprises the steps of forming a suspension of ABT-199 monohydrochloride solid in isopropanol or a mixed solvent of isopropanol and another organic solvent, stirring the mixture for crystallization at a certain temperature, separating and drying the precipitated crystals, and obtaining ABT-199 monohydrochloride Form G. Preferably, the another organic solvent is alkane, cyclic ether, $C_4$ to $C_5$ ester or a mixture thereof, and the temperature is 10 to 60° C.

ABT-199 monohydrochloride Form H, with Cu-Kα radiation, has an X-ray powder diffraction pattern of Form H, expressed as 2θ angles, with the following characteristic peaks: 4.6±0.2°, 8.3±0.2°, 9.5±0.2°, 12.1±0.2°, 12.4±0.2°, 14.5±0.2°, 17.1±0.2°, 18.0±0.2°, 19.0±0.2°, 19.4±0.2°, 20.9±0.2° and 23.1±0.2°.

The invention also provides the preparation method of the ABT-199 monohydrochloride Form H, which comprises the steps of forming a suspension of ABT-199 monohydrochloride solid in n-propanol or a mixed solvent of n-propanol and another organic solvent, stirring the mixture for crystallization at a certain temperature, separating and drying the precipitated crystals, and obtaining ABT-199 monohydrochloride Form H. Preferably, the another organic solvent is water, cyclic ethers, alkanes, $C_4$ to $C_5$ ester or a mixture thereof, and the temperature is from 10 to 60° C.

ABT-199 monohydrochloride Form I, with Cu-Kα radiation, has an X-ray powder diffraction pattern of Form I, expressed as 2θ angles, with the following characteristic peaks: 4.5±0.2°, 8.5±0.2°, 12.1±0.2°, 17.3±0.2°, 18.0±0.2°, 18.3±0.2°, 19.1±0.2°, 19.5±0.2°, 20.9±0.2°, 23.0±0.2°, 26.3±0.2° and 27.1±0.2°.

The invention also provides the preparation method of ABT-199 monohydrochloride Form I, which comprises the steps of forming a suspension of ABT-199 monohydrochloride solid in 2-butyl alcohol or a mixed solvent of 2-butyl alcohol and another organic solvent, stirring the mixture for crystallization at a certain temperature, separating and drying the precipitated crystals, and obtaining ABT-199 monohydrochloride Form I. Preferably, the another organic solvent is alkane, cyclic ether, $C_4$ to $C_5$ ester or a mixture thereof, and the temperature is 10 to 60° C.

ABT-199 monohydrochloride Form J, with Cu-Kα radiation, has an X-ray powder diffraction pattern of Form J, expressed as 2θ angles, with the following characteristic peaks: 4.5±0.2°, 8.1±0.2°, 11.8±0.2°, 12.1±0.2°, 12.3±0.2°, 14.6±0.2°, 17.8±0.2°, 19.0±0.2°, 21.1±0.2°, 23.0±0.2°, 24.7±0.2° and 26.8±0.2°.

The invention also provides the preparation method of ABT-199 monohydrochloride Form J, which comprises the steps of forming a suspension of ABT-199 monohydrochloride solid in n-butanol or a mixed solvent of n-butanol and another organic solvent, stirring the mixture for crystallization at a certain temperature, separating and drying the precipitated crystals, and obtaining ABT-199 monohydrochloride Form J. Preferably, the organic solvent is alkane, cyclic ether, $C_4$ to $C_5$ ester or a mixture thereof, and the temperature is 10 to 60° C.

ABT-199 monohydrochloride Form K, with Cu-Kα radiation, has an X-ray powder diffraction pattern of Form K, expressed as 2θ angles, with the following characteristic peaks: 4.6±0.2°, 8.5±0.2°, 11.8±0.2°, 12.5±0.2°, 13.2±0.2°, 17.4±0.2°, 17.7±0.2°, 19.4±0.2°, 21.4±0.2°, 22.3±0.2°, 23.7±0.2° and 26.9±0.2°.

The invention also provides the preparation method of ABT-199 monohydrochloride Form K, which comprises the steps of forming a suspension of ABT-199 monohydrochloride solid in acetone or a mixed solvent of acetone and another organic solvent, stirring the mixture for crystallization at a certain temperature, separating and drying the precipitated crystals, and obtaining ABT-199 monohydrochloride Form K. Preferably, the organic solvent is alkane, $C_4$ to $C_5$ ester, water or a mixture thereof, and the temperature is 10 to 50° C.

ABT-199 monohydrochloride Form L, with Cu-Kα radiation, has an X-ray powder diffraction pattern of Form L, expressed as 2θ angles, with the following characteristic peaks: 4.5±0.2°, 7.6±0.2°, 8.3±0.2°, 14.2±0.2°, 15.7±0.2°, 16.8±0.2°, 17.9±0.2°, 18.7±0.2°, 19.1±0.2°, 21.2±0.2°, 22.2±0.2° and 25.7±0.2°.

The invention also provides the preparation method of ABT-199 monohydrochloride Form L, which comprises the steps of forming a suspension of ABT-199 monohydrochloride solid in 1,4-dioxane or a mixed solvent of 1,4-dioxane and another organic solvent, stirring the mixture for crystallization at a certain temperature, separating and drying the precipitated crystals, and obtaining ABT-199 monohydrochloride Form L. Preferably, the organic solvent is alkane, $C_4$ to $C_5$ ester or a mixture thereof, and the temperature is 10 to 60° C.

ABT-199 monohydrochloride Form M, with Cu-Kα radiation, has an X-ray powder diffraction pattern of Form M, expressed as 2θ angles, with the following characteristic peaks: 4.6±0.2°, 8.3±0.2°, 11.9±0.2°, 12.3±0.2°, 17.2±0.2°, 17.8±0.2°, 18.3±0.2°, 19.1±0.2°, 21.0±0.2°, 22.3±0.2°, 23.5±0.2° and 27.0±0.2°.

The invention also provides the preparation method of ABT-199 monohydrochloride Form M, which comprises the steps of forming a suspension of ABT-199 monohydrochloride solid in tetrahydrofuran or a mixed solvent of tetrahydrofuran and another organic solvent, stirring the mixture for crystallization at a certain temperature, separating and drying the precipitated crystals, and obtaining the ABT-199 monohydrochloride Form M. Preferably, the organic solvent is alkane, $C_4$ to $C_5$ ester, water or a mixture thereof, and the temperature is from 10 to 60° C.

ABT-199 monohydrochloride Form N, with Cu-Kα radiation, has an X-ray powder diffraction pattern of Form N, expressed as 2θ angles, with the following characteristic peaks: 4.5±0.2°, 5.7±0.2°, 7.5±0.2°, 8.5±0.2°, 10.5±0.2°, 12.1±0.2°, 17.4±0.2°, 18.0±0.2°, 18.3±0.2°, 19.2±0.2°, 19.5±0.2° and 20.9±0.2°.

The invention also provides the preparation method of ABT-199 monohydrochloride Form N, which comprises the steps of forming a suspension of ABT-199 monohydrochloride solid in a solvent, stirring the mixture for crystallization at a certain temperature, separating and drying the precipitated crystals, and obtaining ABT-199 monohydrochloride Form N. Preferably, the solvent is a mixed solvent of methanol and water, and the temperature is 10 to 60° C.

Compared with the known ABT-199 monohydrochloride forms, Form A, Form B, Form C, Form D, Form E, Form F, Form G, Form H, Form I, Form J, Form K, Form L, Form M, Form N of ABT-199 monohydrochloride and ABT-199 dihydrochloride Form 1 in the present invention have one or more improved properties, such as higher crystallinity, better solubility and dissolution rate, better crystalorphology, better thermal stability and storage stability, better fluidity and better processability, easier preparation at room temperature or high temperature, and/or convenient product industrialization.

Some terms are defined below for the preparation methods of Form A, Form B, Form C, Form D, Form E, Form F, Form G, Form H, Form I, Form J, Form K, Form L, Form M, Form N of ABT-199 monohydrochloride and ABT-199 dihydrochloride Form 1 in the present invention.

Unless particularly specified, "room temperature" refers to a temperature of 10 to 30° C.

The "chlorinated alkane" refers to dichloromethane or chloroform.

The "cyclic ether" refers to tetrahydrofuran or 1,4-dioxane.

The "stirring" can be performed by routine methods in the field, such as magnetic stirring and mechanical stirring, and the stirring speed is 50 to 1800 rpm, preferably 300 to 900 rpm.

The "separation" can be performed by routine methods in the field, such as centrifugation or filtration. The preferred method is filtration under reduced pressure, which is generally carried out by suction filtration at a pressure of less than atmospheric pressure at room temperature, preferably at a pressure of less than 0.09 MPa.

The "filtering" is generally performed by suction filtration at a pressure of less than atmospheric pressure at room temperature, preferably at a pressure of less than 0.09 MPa.

The "centrifugation" can be done by placing the sample to be separated in a centrifuge tube and centrifuged at a rate of 6000 rpm until all the solids settled to the bottom of the centrifuge tube.

"Drying" can be performed by routine methods in the field, such as drying at room temperature, blast drying and drying under reduced pressure. Drying is performed under reduced pressure or atmospheric pressure, preferably less than 0.09 MPa. Drying instruments and methods are unrestricted, and may be fume hood, blast oven, spray drying fluidized bed drying or vacuum oven.

In the present invention, the term "crystalline form" refers to a compound's unique ordered molecular arrangement or configuration within the crystalline lattice as characterized by X-ray powder diffraction pattern. It is known to those skilled in the field that the experimental error depends on instrumental conditions, sample preparation and sample purity. The 2θ angle of the peaks in the XRPD pattern may change with the change of instrument and/or samples. The difference of peak position may vary by 1°, 0.8°, 0.5°, 0.3°, 0.1° and the like depending on the instruments and samples, and ±0.2° is usually allowed. Therefore the difference in peak angle should be considered with other factors. The relative intensity of peaks may change with the change of sample, sample preparation, and other experimental conditions. Therefore, the order of peak intensities should not be regarded as the only or the key factor. Due to the effect of experimental factors including sample height, peak position may shift. Generally, a small amount of peak shifting is acceptable. Hence, it is easily understood for those skilled in the field that any crystalline form having the same or similar X-ray powder diffraction pattern as that of the crystalline form in the present invention should be within the scope of the present invention. "Single crystalline form" refers to a crystalline form confirmed by X-ray powder diffraction as a single form.

In the present invention, the forms of ABT-199 monohydrochloride or dihydrochloride are substantially pure, i.e., substantially free of any other crystalline or amorphous forms. As used herein, "substantially pure" when used in reference to a new crystalline form means that the new crystalline form comprises at least 80% by weight of the present compound crystals, more preferably at least 90% by weight, especially at least 95% (Weight), especially at least 99% by weight.

Furthermore, the present invention provides a pharmaceutical composition comprising a therapeutically and/or prophylactically effective amount of one or more novel crystalline forms of ABT-199 monohydrochloride and/or dihydrochloride of the present invention or novel crystalline forms of ABT-199 monohydrochloride and/or dihydrochloride prepared by the processes in the present invention, and at least one pharmaceutically acceptable carrier. Among them, the new crystalline forms of ABT-199 hydrochloride include Form A, Form B, Form C, and Form 1. In addition, the pharmaceutical composition may further comprise other pharmaceutically acceptable ABT-199 hydrochloride Forms (such as Form D, Form E, Form F, Form G, Form H, Form I, Form J, Form K, Form L, Form M and Form N) or amorphous ABT-199 hydrochloride.

The excipients in the pharmaceutical compositions are well known to those skilled in the field, and the excipient species, usage, and the amount in use are well known to those skilled in the field. Excipients include, for example, saccharides, cellulose and its derivatives, starch or modified starch, solid inorganics such as calcium phosphate, dicalcium phosphate, hydroxyapatite, calcium sulfate, calcium carbonate, semi-solid such as lipid or paraffin, adhesives such as microcrystalline cellulose, ethyl cellulose, hydroxymethyl cellulose, hydroxypropyl methyl cellulose, hydroxyethyl cellulose, glidants such as colloidal silica, light anhydrous silicic acid, crystalline cellulose, talc or magnesium stearate, disintegrants such as sodium starch glycolate, crospovidone, croscarmellose, sodium carboxymethylcellulose, dry corn starch, lubricants such as stearic acid, magnesium stearate, sodium stearyl fumarate, and polyethylene glycol.

The administration route of the pharmaceutical composition includes oral administration, intravenous or subcutaneous injection, intra-tissue injection, transdermal administration, rectal administration, and intranasal administration, etc.

Depending on the route of administration or needs, the pharmaceutical composition may be prepared as certain dosage forms, such as solid or liquid. Solid oral dosage forms, include for example tablets, granules, powders, pills, and capsules; liquid oral dosage forms include for example solutions, syrups, suspensions, dispersions, and emulsions; injectable preparations include solutions, dispersions and lyophilizate. The formulation may be suitable for immediate-release, sustained-release or controlled-release of the active ingredient. The formulation may be a regular, dispersible, chewable, orally soluble or rapidly dissolving form.

The pharmaceutical composition may be prepared by the methods commonly known to those skilled in the art. When preparing a pharmaceutical composition, Form A, Form B, Form C or Form 1 in the present invention is mixed with one or more pharmaceutically acceptable excipients, optionally mixed with pharmaceutically acceptable other forms or amorphous ABT-199 monohydrochloride and ABT-199 dihydrochloride, optionally with one or more other pharmaceutically active ingredients. The solid dosage form can be prepared by direct mix or granulation methods.

Furthermore, the present invention provides the use of one or more novel forms of ABT-199 monohydrochloride and/or ABT-199 dihydrochloride in the present invention in the manufacture of a medicament for treating and/or preventing one or more disease associated with over-expression of anti-apoptotic BCL-2 family proteins, and the novel forms include ABT-199 monohydrochloride Form A, Form B, Form C, Form D, Form E, Form F, Form G, Form H, Form I, Form J, Form K, Form L, Form M, and Form N, and ABT-199 dihydrochloride Form 1 in the present invention.

Further, the present invention provides a method for treating and/or preventing one or more diseases associated with overexpression of anti-apoptotic BCL-2 family proteins. The method comprises administering to a patient in need thereof a therapeutically and/or prophylactically effective amount of novel forms of ABT-199 monohydrochloride and novel forms of ABT-199 dihydrochloride or a combination thereof or a pharmaceutical composition thereof, and the new crystalline forms of the ABT-199 hydrochloride includes Form A, Form B, Form C, Form D, Form E, Form F, Form G, Form H, Form I, Form J, Form K, Form L, Form M and Form N, and ABT-199 dihydrochloride Form 1 in the present invention. Such patients include, but not limited to mammals.

DETAILED DESCRIPTION OF EMBODIMENTS

Figure 1:
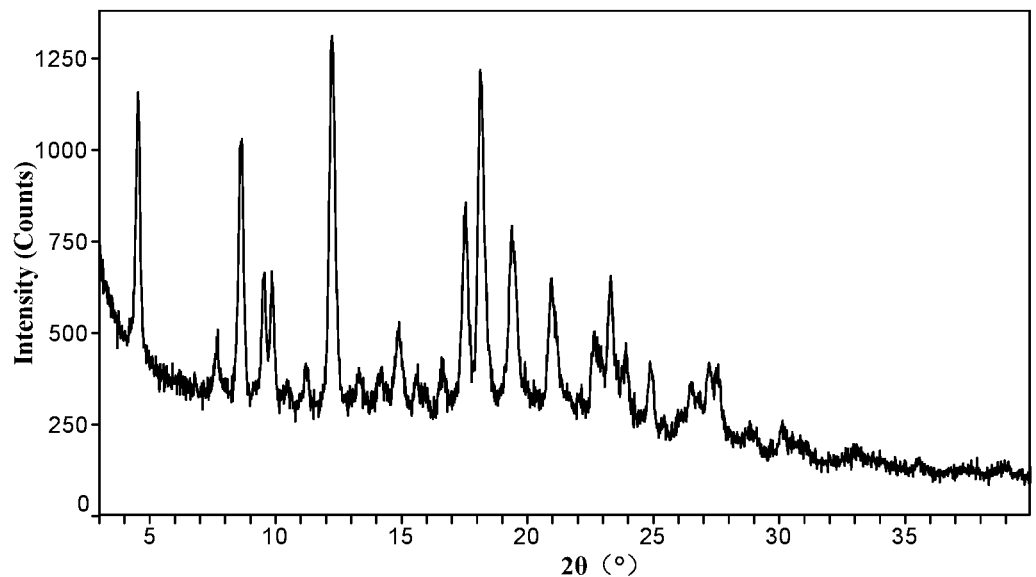
FIG. 1 is an X-ray powder diffraction pattern of a known hydrochloride Form II prepared according to the method described in Example 14 in patent application CN103328474A.

The present invention is further illustrated by the following examples, but these examples do not constitute any limitation to the present invention.

Instruments and Characterization Methods

The instrument used for collecting x-ray powder diffraction (XRPD) patterns was Bruker D8 Advance diffractometer. The samples were tested at room temperature under the following conditions: 2θ scan range, 3-40°; step size, 0.02°/step; speed, 0.2 s/step.

Differential thermal analysis data was collected on TA Instruments Q200 MDSC. The procedure was as follows: 1-10 mg sample was placed in an aluminum pan with a pin-holed lid, and the sample temperature was increased at 10° C./min to 230 to 250° C. under the protection of dry N2 purge flowing at 40 mL/min.

Thermogravimetric analysis data was collected on TA Instruments Q500 TGA. The procedure was as follows: 5-15 mg sample was placed in a platinum pan, and the sample temperature was increased at 10° C./min to 300° C. under the protection of dry N2 purge flowing at 40 mL/min, wherein the analysis was done in a high resolution manner.

Infrared spectrometry (IR) data was collected on BrukerTensor 27 equipped with an attenuated total reflection (ATR), the infrared spectra were collected at 600-4000 cm−1.

Nuclear magnetic resonance spectroscopy data ($^1$H NMR) was collected using a Bruker Avance II DMX 300 MHZ NMR spectrometer. A sample of 1-5 mg was weighed and dissolved in a nuclear magnetic tube with about 0.5 mL of deuterated dimethyl sulfoxide.

High performance liquid chromatography (HPLC) data was collected using Ultimate 3000 with an external standard method was used.

The Examples were conducted at room temperature unless otherwise noted.

All reagents used in the Examples are commercially available unless otherwise noted.

Preparation Example 1

ABT-199 can be prepared according to the method described in the example of patent application CN103328474A for synthesis of compound 1.

The operating procedures were detailed as follows.

A mixture of 4-fluoro-3-nitrobenzenesulfonamide (2.52 g), 1-(tetrahydropyran-4-yl)methylamine (1.32 g), and triethylamine (1.16 g) in tetrahydrofuran (35 mL) were stirred overnight, neutralized with concentrated HCl and concentrated. The residue was suspended in ethyl acetate and the precipitates were collected, washed with water and dried to provide 3-nitro-4-((tetrahydro-2H-pyran-4-yl)methylamino) benzenesulfonamide.

To a suspension of hexane washed NaH (20 g) in dichloromethane (809 mL) was added 5,5-dimethyl-2-methoxycarbonylcyclohexanone (44.5 g) dropwise at 0° C. After stirring for 30 minutes, the mixture was cooled to −78° C., and trifluoroacetic anhydride (46 mL) was added. The reaction mixture was warmed to room temperature and stirred for 24 hours. The organic layer was washed with brine, dried ($Na_2SO_4$), filtered, and concentrated to give methyl 4,4-dimethyl-2-(trifluoromethylsulfonyloxy)cyclohex-1-enecarboxylate.

Methyl 4,4-dimethyl-2-(trifluoromethylsulfonyloxy)cyclohex-1-enecarboxylate (71.84 g), 4-chlorophenylboronic acid (37.27 g), CsF (74 g) and tetrakis(triphenylphosphine) palladium(0) (2.3 g) in 2:1 dimethoxyethane/methanol (600 mL) were heated to 70° C. for 24 hours. The mixture was concentrated. Ether (4×230 mL) was added and the mixture was filtered. The combined ether solution was concentrated to give methyl 2-(4-chlorophenyl)-4,4-dimethylcyclohex-1-enecarboxylate.

To a mixture of $LiBH_4$ (15 g), methyl 2-(4-chlorophenyl)-4,4-dimethylcyclohex-1-enecarboxylate (62.2 g) and ether (460 mL), was added methanol (30 mL) slowly by syringe. The mixture was stirred at room temperature for 24 hours. The reaction was quenched with 1N HCl with ice-cooling. The mixture was diluted with water and extracted with ether (3×116 mL). The extracts were dried ($Na_2SO_4$), filtered, and concentrated. The crude product was chromatographed on silica gel with 0-30% ethyl acetate/hexane to give (2-(4-chlorophenyl)-4,4-dimethylcyclohex-1-enyl)methanol.

Mesyl Chloride (8.7 mL) was added via syringe to (2-(4-chlorophenyl)-4,4-dimethylcyclohex-1-enyl)methanol (33.9 g) and triethylamine (35 mL) in $CH_2Cl_2$ (580 mL) at 0° C., and the mixture was stirred for 1 minute. N-t-butoxycarbonylpiperazine (25 g) was added and the mixture was stirred at room temperature for 24 hours. The suspension was washed with brine, dried, ($Na_2SO_4$), filtered, and concentrated. The crude product was chromatographed on silica gel with 10-20% ethyl acetate/hexane to give tert-butyl 4-((2-(4-chlorophenyl)-4,4-dimethylcyclohex-1-enyl)methyl)piperazine-1-carboxylate.

Tert-butyl 4-((2-(4-chlorophenyl)-4,4-dimethylcyclohex-1-enyl)methyl)piperazine-1-carboxylate (231 mg) and triethylsilane (1.2 mL) were stirred in dichloromethane (17 mL) and trifluoroacetic acid (17 mL) for 1 hour. The mixture was concentrated, taken up in ethyl acetate, washed twice with $NaH_2PO_4$, and brine, and dried ($Na_2SO_4$), filtered and concentrated to give 1-((2-(4-chlorophenyl)-4,4-dimethylcyclohex-1-enyl)methyl)piperazine.

To a mixture of 5-bromo-1H-pyrrolo[2,3-b]pyridine (15.4 g) in tetrahydrofuran (290 mL) was added 1M lithium hexamethyldisilazide in tetrahydrofuran (100 mL), and after 10 minutes, TIPS-Cl (triisopropylchlorosilane) (21 mL) was added. The mixture was stirred at room temperature for 24 hours. The reaction was diluted with ether, and the resulting solution was washed twice with water. The extracts were dried ($Na_2SO_4$), filtered, and concentrated. The crude product was chromatographed on silica gel with 10% ethyl acetate/hexanes to give 5-bromo-1-(triisopropylsilyl-1H-pyrrolo[2,3-b]pyridine.

To a mixture of 5-bromo-1-(triisopropylsilyl-1H-pyrrolo [2,3-b]pyridine (28 g) in tetrahydrofuran (580 mL) at −78° C. was added 2.5M BuLi (35 mL). After 2 minutes, trimethylborate (13 mL) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (230 mL) at 0° C., and 1M NaOH (80 mL) was added, followed by 30% $H_2O_2$ (9.7 mL), and the solution was stirred for 1 hour. $Na_2S_2O_3$ (11.6 g) was added, and the pH was adjusted to 4-5 with concentrated HCl and solid $NaH_2PO_4$. The solution was extracted twice with ethyl acetate, and the combined extracts were washed with brine, dried (Na$_2$SO$_4$), filtered, and concentrated. The crude product was chromatographed on silica gel with 5-25% ethyl acetate/hexanes to give 1-(triisopropylsilyl)-1H-pyrrolo[2,3-b]pyridin-5-ol.

A mixture of 1-(triisopropylsilyl)-1H-pyrrolo[2,3-b]pyridin-5-ol (9.8 g), methyl 2,4-difluorobenzoate (8.1 g), and K$_3$PO$_4$ (10.77 g) in diglyme (46 mL) at 115° C. was stirred for 24 hours. The reaction was cooled, diluted with ether (600 mL), and washed twice with water, and brine, and concentrated. The crude product was chromatographed on silica gel with 2-50% ethyl acetate/hexanes to give methyl 2-(1H-pyrrolo[2,3-b]pyridin-5-yloxy)-4-fluorobenzoate.

A mixture of methyl 2-(1H-pyrrolo[2,3-b]pyridin-5-yloxy)-4-fluorobenzoate (1.79 g), 1-((2-(4-chlorophenyl)-4,4-dimethylcyclohex-1-enyl)methyl)piperazine (2.80 g), and HK$_2$PO$_4$ (1.64 g) in dimethylsulfoxide (23 mL) at 135° C. was stirred for 24 hours. The reaction was cooled, diluted with ether (460 mL), and washed with 3×1M NaOH, and brine, and concentrated. The crude product was chromatographed on silica gel with 10-50% ethyl acetate/hexanes to give methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate.

Methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate (231 mg) in dioxane (11.6 mL) and 1M NaOH (6.9 mL) at 50° C. was stirred for 24 hours. The reaction system was cooled, added to NaH$_2$PO$_4$ solution, and extracted three times with ethyl acetate. The combined extracts were washed with brine, and concentrated to give the pure product.

2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic acid (3.92 g), 3-nitro-4-((tetrahydro-2H-pyran-4-yl)methylamino)benzenesulfonamide (2.16 g), 1-ethyl-3-[3-(dimethylamino)propyl]-carbodiimide hydrochloride (2.76 g), and 4-dimethylaminopyridine (1.26 g) were stirred in CH$_2$Cl$_2$ (46 mL) for 24 hours. The reaction system was cooled and chromatographed on silica gel with 25-100% ethyl acetate/hexanes, then with 10% methanol/ethyl acetate with 1% acetic acid, to give the product (1.81 g) as a solid.

$^1$HNMR (300 MHz, DMSO-d6): 11.65 (brs, 1H), 8.55 (brs, 1H), 8.04 (d, 1H), 7.89 (dd, 1H), 7.51 (m, 3H), 7.33 (d, 2H), 7.08 (m, 1H), 7.04 (d, 2H), 6.68 (dd, 1H), 6.39 (d, 1H), 6.19 (d, 4H), 3.84 (m, 1H), 3.30 (m, 4H), 3.07 (m, 4H), 2.73 (m, 2H), 2.18 (m, 6H), 1.95 (m, 2H), 1.61 (dd, 2H), 1.38 (m, 2H) 1.24 (m, 4H), 0.92 (s, 6H), Displayed as known ABT-199.

Preparation Example 2

The known ABT-199 hydrochloride hydrate form (i.e. Form II in the present invention) can be prepared according to the method described in Examples 14 to 15 in patent application CN103328474A.

ABT-199 (free base) solid 2.5 g was suspended in 100 mL acetonitrile. While stirring, 321 mg concentrated hydrochloric acid which was diluted with 1.5 mL acetonitrile was dripped into the suspension. The reactants reacted rapidly and formed a transparent solution, followed by the precipitation of light yellow solid. The light yellow solids were exposed in the air to obtain ABT-199 hydrochloride.

The X-ray powder diffraction pattern of ABT-199 hydrochloride is shown in FIG. 1, which is basically the same as that of ABT-199 hydrochloride hydrate hydrate in patent application CN103328474A.

Example 1

In 100 mg ABT-199 hydrochloride prepared in Preparation Example 2 was added 3 mL ethanol to form a suspension. After stirred at room temperature for 3 days, the suspension was filtered under reduced pressure, and the solids were dried under vacuum at 40° C. for 10 hours to obtain 98 mg ABT-199 monohydrochloride Form A.

Figure 2:
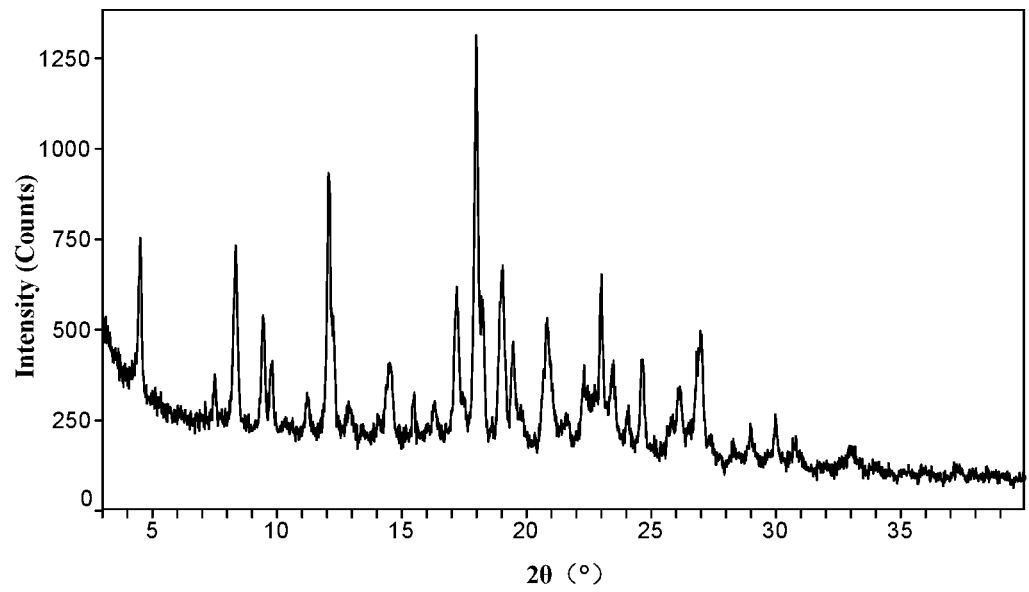
FIG. 2 is an X-ray powder diffraction pattern of ABT-199 monohydrochloride Form A of Example 1 of the present invention.
Figure 3:
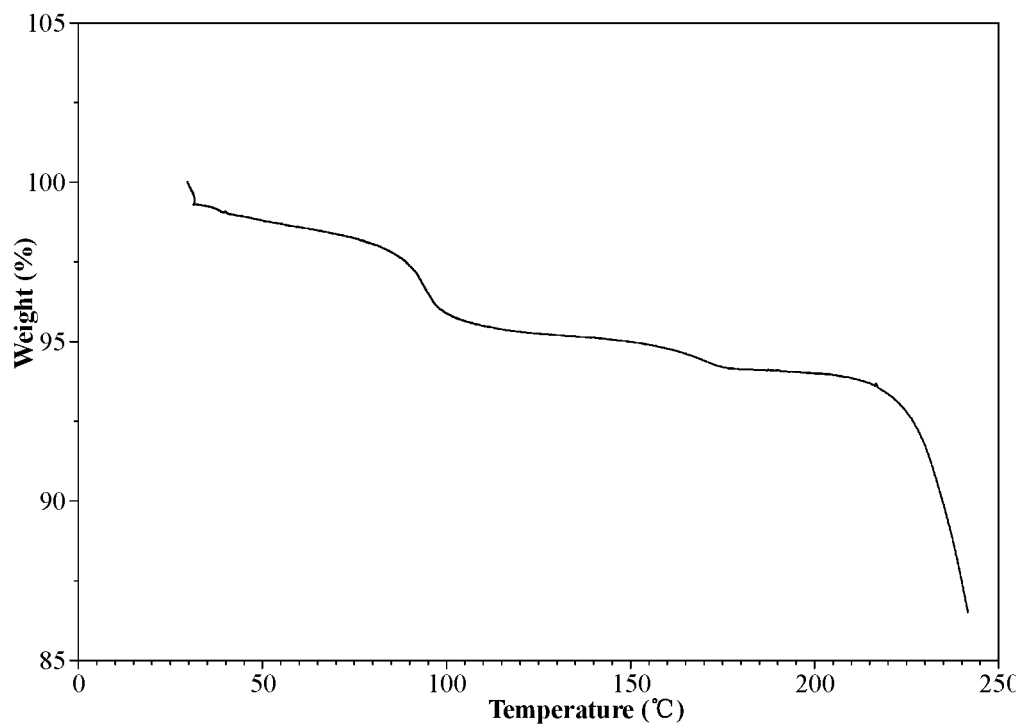
FIG. 3 is a TGA pattern of ABT-199 monohydrochloride Form A of Example 1 of the present invention.
Figure 4:
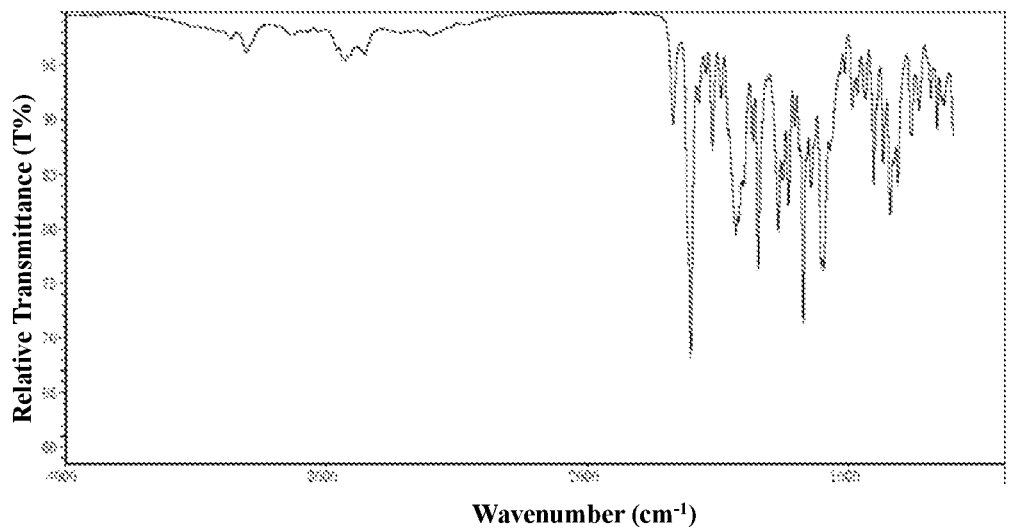
FIG. 4 is an IR spectrum of ABT-199 monohydrochloride Form A of Example 1 of the present invention.

Its X-ray powder diffraction pattern is shown in FIG. 2.
Its TGA pattern is shown in FIG. 3.
Its IR spectrum is shown in FIG. 4.

Example 2

In 50 mg ABT-199 hydrochloride prepared in Preparation Example 2 were added 0.5 mL ethanol and 0.5 mL water to form a suspension, and the mixture was stirred at room temperature for 7 days, then filtered under reduced pressure, and the solids were dried under vacuum at 30° C. for 24 hours to obtain 48 mg ABT-199 monohydrochloride Form A.

Example 3

In 20 mg ABT-199 hydrochloride prepared in Preparation Example 2 were added 0.5 mL ethanol and 0.5 mL n-heptane to form a suspension, and the mixture was stirred at room temperature for 5 days, then filtered under reduced pressure, and the solids were dried under vacuum at 10° C. for 10 hours to obtain 19 mg ABT-199 monohydrochloride Form A.

Example 4

In 10 mg ABT-199 hydrochloride prepared in Preparation Example 2 were added 0.5 mL ethanol and 0.5 mL methyl tert-butyl ether to form a suspension, the suspension was stirred at room temperature for 1 day, and then filtered under reduced pressure, and the solids were dried at 40° C. for 16 hours under vacuum, 9 mg ABT-199 monohydrochloride Form A was obtained.

Example 5

In 10 mg ABT-199 hydrochloride prepared in Preparation Example 2 were added 0.5 mL ethanol and 0.5 mL ethyl acetate to form a suspension, the suspension was stirred at 60° C. for 2 days, and then filtered under reduced pressure, and the solids were dried at 25° C. for 16 hours under vacuum, 7 mg ABT-199 monohydrochloride Form A was obtained.

Example 6

In 20 mg ABT-199 hydrochloride prepared in Preparation Example 2 were added 0.4 mL ethanol and 0.6 mL dichloromethane to form a suspension, and the mixture was stirred at 50° C. for 1 day, filtered under reduced pressure, and the solids were dried at 60° C. for 48 hours under vacuum, 15 mg ABT-199 monohydrochloride Form A was obtained.

Example 7

In 20 mg ABT-199 hydrochloride prepared in Preparation Example 2 were added 0.1 mL ethanol, 0.1 mL isopropyl acetate and 0.1 mL n-heptane to form a suspension, and the mixture was stirred at room temperature for 4 days, and then filtered under reduced pressure, and the solids were dried at 55° C. for 20 hours under vacuum to obtain 17 mg ABT-199 monohydrochloride Form A.

Example 8

In 20 mg ABT-199 hydrochloride prepared in Preparation Example 2 were added 0.2 mL ethanol, 0.1 mL tetrahydrofuran and 0.2 mL n-heptane to form a suspension, and the mixture was stirred at room temperature for 5 days, and then filtered under reduced pressure, and the solids were dried at 40° C. for 24 hours under vacuum to obtain 19 mg ABT-199 monohydrochloride Form A.

Example 9

In 20 mg ABT-199 hydrochloride prepared in Preparation Example 2 were added 0.1 mL ethanol, 0.2 mL acetonitrile and 0.2 mL n-heptane to form a suspension, and the mixture was stirred at room temperature for 2 days, and then filtered under reduced pressure, and the solids were dried at 60° C. for 16 hours under vacuum to obtain 18 mg ABT-199 monohydrochloride Form A.

Example 10

In 30 mg ABT-199 hydrochloride prepared in Preparation Example 2 were added 0.1 mL ethanol, 0.1 mL chloroform and 0.2 mL methylcyclohexane to form a suspension, and the mixture was stirred at 40° C. for 3 days, and then filtered under reduced pressure, and the solids were dried at 40° C. for 36 hours under vacuum to obtain 25 mg ABT-199 monohydrochloride Form A.

Example 11

In 60 mg ABT-199 hydrochloride prepared in Preparation Example 2 were added 0.2 mL ethanol, 0.2 mL ether and 0.2 mL n-heptane to form a suspension, and the mixture was stirred at 60° C. for 1 day, and then filtered under reduced pressure, and the solids were dried at 60° C. for 16 hours under vacuum to obtain 47 mg ABT-199 monohydrochloride Form A.

Example 12

In 20 mg ABT-199 hydrochloride prepared in Preparation Example 2 were added 0.2 mL ethanol, 0.2 mL 1,4-dioxane and 0.2 mL n-heptane to form a suspension, and the mixture was stirred at 40° C. for 5 days, and then filtered under reduced pressure, and the solids were dried at 40° C. for 24 hours under vacuum to obtain 17 mg ABT-199 monohydrochloride Form A.

The samples prepared in Examples 2 to 12 had the same or similar XRPD patterns, TGA patterns, and IR spectra (not shown) as those in Example 1, indicating that the samples of Examples 2 to 12 had identical crystalline form as the samples in Example 1.

Example 13

The ABT-199 monohydrochloride Form A of the present invention was heated from room temperature to the desolvation temperature, 130° C., at a heating rate of 5° C./min, held at 130° C. for 20 minutes to completely remove the solvent, and then cooled to room temperature at a cooling rate of 20° C./min to obtain ABT-199 monohydrochloride Form B.

Figure 5:
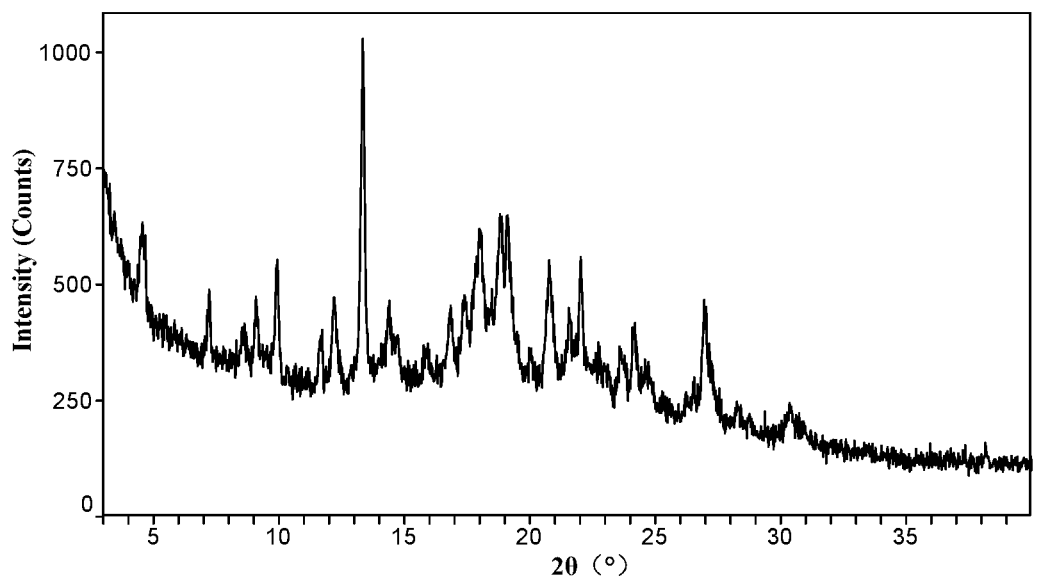
FIG. 5 is an X-ray powder diffraction pattern of ABT-199 monohydrochloride Form B of Example 13 of the present invention
Figure 6:
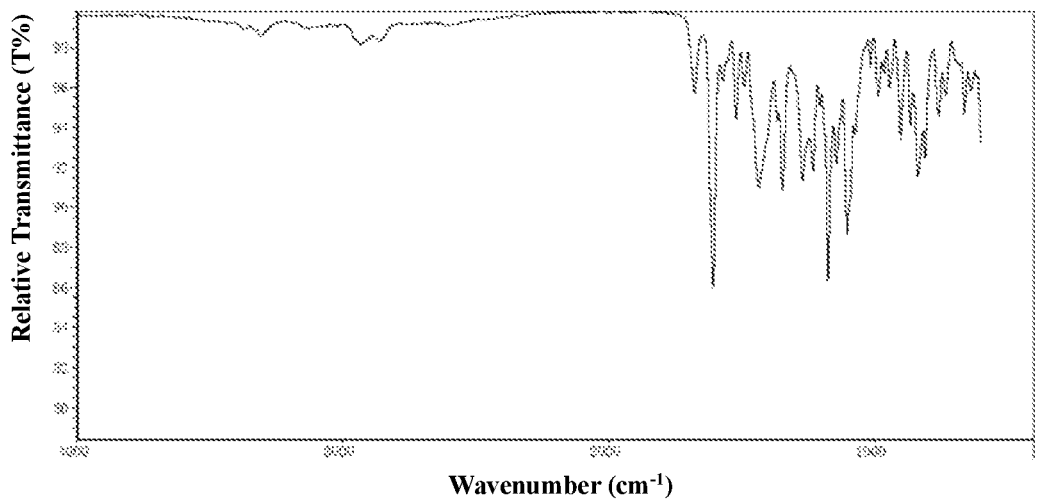
FIG. 6 is an IR spectrum of ABT-199 monohydrochloride Form B of Example 13 of the present invention.

Its X-ray powder diffraction pattern is shown in FIG. 5.
Its IR spectrum is shown in FIG. 6.

Example 14

The ABT-199 monohydrochloride Form A of the present invention was heated from room temperature to the desolvation temperature, 130° C., at a heating rate of 10° C./min, held at 130° C. for 10 minutes to completely remove the solvent, and then cooled to room temperature at a cooling rate of 10° C./min to obtain ABT-199 monohydrochloride Form B.

Example 15

The ABT-199 monohydrochloride Form A of the present invention was heated from room temperature to the desolvation temperature, 130° C., at a heating rate of 8° C./min, held at 130° C. for 25 minutes to completely remove the solvent, and then cooled to room temperature at a cooling rate of 15° C./min to obtain ABT-199 monohydrochloride Form B.

Example 16

The ABT-199 monohydrochloride Form A of the present invention was heated from room temperature to the desolvation temperature, 130° C., at a heating rate of 20° C./min, held at 130° C. for 35 minutes to completely remove the solvent, and then cooled to room temperature at a cooling rate of 5° C./min to obtain ABT-199 monohydrochloride Form B.

Example 17

The ABT-199 monohydrochloride Form A of the present invention was heated from room temperature to the desolvation temperature, 130° C., at a heating rate of 15° C./min, held at 130° C. for 5 minutes to completely remove the solvent, and then cooled to room temperature at a cooling rate of 5° C./min to obtain ABT-199 monohydrochloride Form B.

Example 18

The ABT-199 monohydrochloride Form A of the present invention was placed at 140° C. for 30 minutes until the solvent was completely removed, and then was directly placed at room temperature to obtain ABT-199 monohydrochloride Form B.

Example 19

The ABT-199 monohydrochloride Form A of the present invention was placed at 150° C. for 20 minutes until the solvent was completely removed, and then was directly placed at room temperature to obtain ABT-199 monohydrochloride Form B.

Example 20

The ABT-199 monohydrochloride Form A of the present invention was placed at 145° C. for 10 minutes until the solvent was completely removed, and then was directly placed at room temperature to obtain ABT-199 monohydrochloride Form B.

Example 21

The ABT-199 monohydrochloride Form A of the present invention was placed at 130° C. for 40 minutes until the solvent was completely removed, and then was directly placed at room temperature to obtain ABT-199 monohydrochloride Form B.

Example 22

The ABT-199 monohydrochloride Form II was heated from room temperature to the desolvation temperature, 130° C., at a heating rate of 5° C./min, held at 130° C. for 20 minutes to completely remove the solvent, and then cooled to room temperature at a cooling rate of 20° C./min to obtain ABT-199 monohydrochloride Form B.

Example 23

The ABT-199 monohydrochloride Form II was heated from room temperature to the desolvation temperature, 130° C., at a heating rate of 10° C./min, held at 130° C. for 10 minutes to completely remove the solvent, and then cooled to room temperature at a cooling rate of 10° C./min to obtain ABT-199 monohydrochloride Form B.

Example 24

The ABT-199 monohydrochloride Form II was heated from room temperature to the desolvation temperature, 130° C., at a heating rate of 8° C./min, held at 130° C. for 25 minutes to completely remove the solvent, and then cooled to room temperature at a cooling rate of 15° C./min to obtain ABT-199 monohydrochloride Form B.

Example 25

The ABT-199 monohydrochloride Form II was heated from room temperature to the desolvation temperature, 130° C., at a heating rate of 20° C./min, held at 130° C. for 35 minutes to completely remove the solvent, and then cooled to room temperature at a cooling rate of 5° C./min to obtain ABT-199 monohydrochloride Form B.

Example 26

The ABT-199 monohydrochloride Form II was heated from room temperature to the desolvation temperature, 130° C., at a heating rate of 15° C./min, held at 130° C. for 5 minutes to completely remove the solvent, and then cooled to room temperature at a cooling rate of 5° C./min to obtain ABT-199 monohydrochloride Form B.

Example 27

The ABT-199 monohydrochloride Form II was placed at 140° C. for 30 minutes until the solvent was completely removed, and then was directly placed at room temperature to obtain ABT-199 monohydrochloride Form B.

Example 28

The ABT-199 monohydrochloride Form II was placed at 150° C. for 20 minutes until the solvent was completely removed, and then was directly placed at room temperature to obtain ABT-199 monohydrochloride Form B. Example 29

The ABT-199 monohydrochloride Form II was placed at 145° C. for 10 minutes until the solvent was completely removed, and then was directly placed at room temperature to obtain ABT-199 monohydrochloride Form B.

Example 30

The ABT-199 monohydrochloride Form II was placed at 130° C. for 40 minutes until the solvent was completely removed, and then was directly placed at room temperature to obtain ABT-199 monohydrochloride Form B.

The samples prepared in Examples 14 to 30 had the same or similar XRPD patterns and IR spectra (not shown) as those of Example 13, indicating that the samples of Examples 14-30 had the same crystalline form as the sample of Example 13.

Example 31

In 100 mg ABT-199 hydrochloride prepared in Preparation Example 2 was added 2 mL methanol to form a suspension, and the mixture was stirred at room temperature for 3 days, and then filtered under reduced pressure, and the solids were dried at 40° C. for 10 hours under vacuum to obtain 98 mg ABT-199 monohydrochloride Form C.

Figure 7:
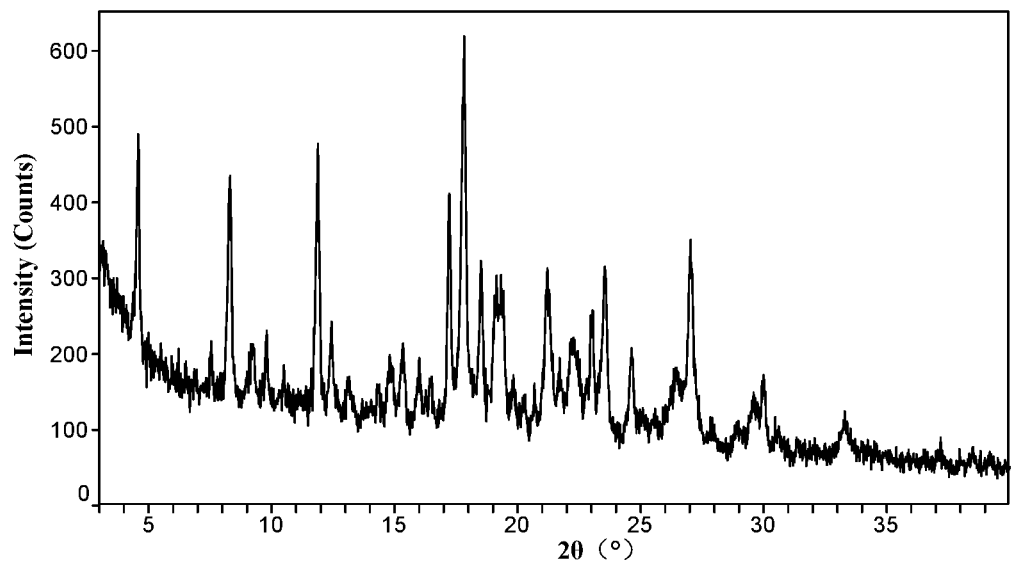
FIG. 7 is an X-ray powder diffraction pattern of ABT-199 monohydrochloride Form C of Example 31 of the present invention
Figure 8:
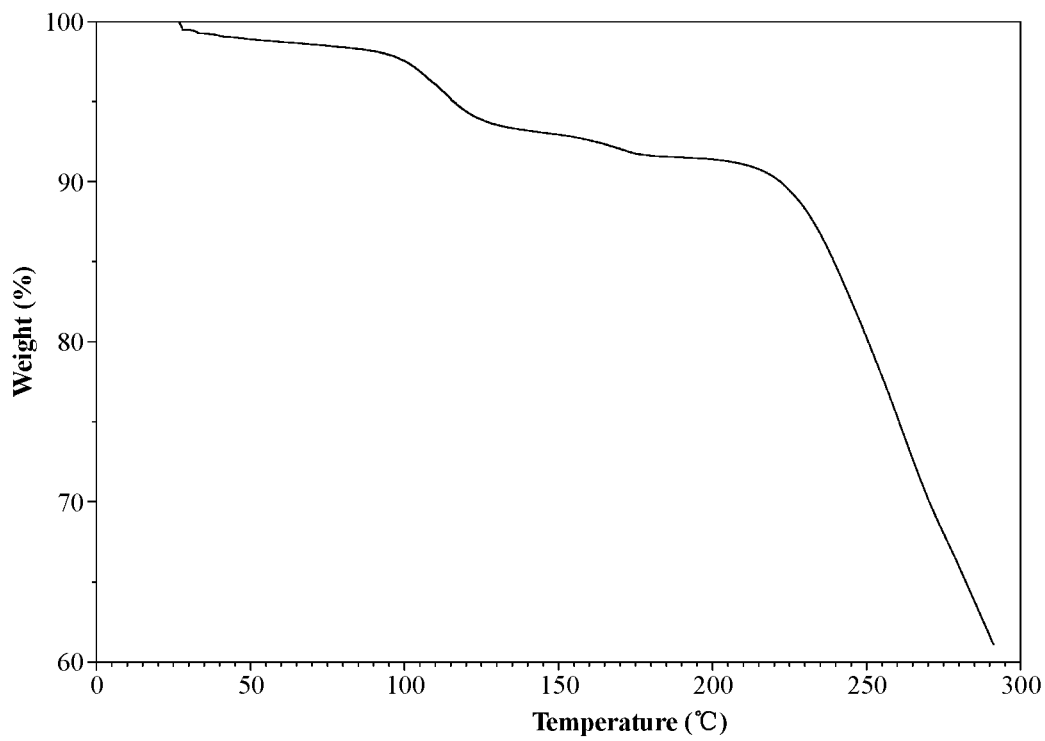
FIG. 8 is a TGA pattern of ABT-199 monohydrochloride Form C of Example 31 of the present invention
Figure 9:
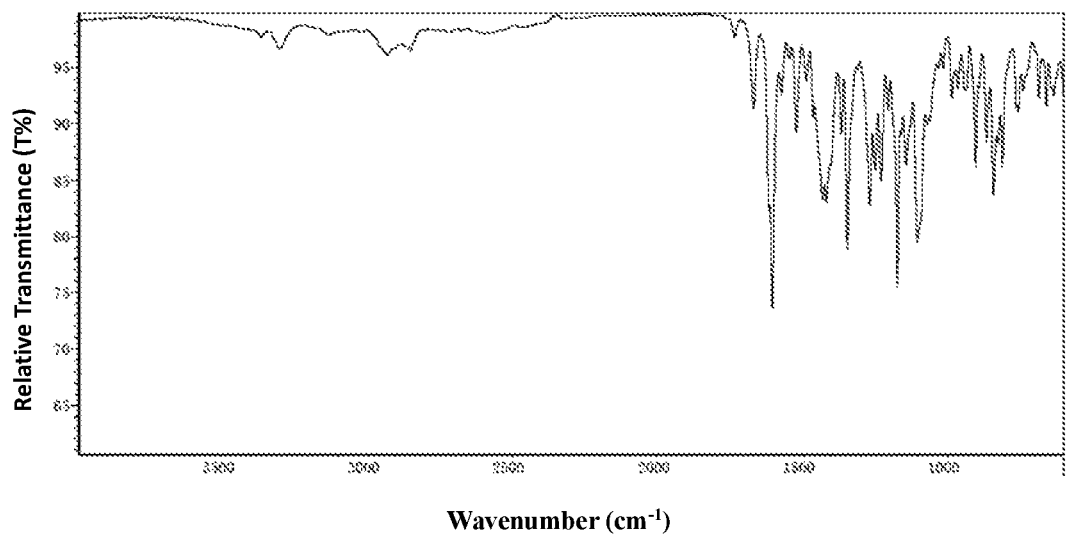
FIG. 9 is an IR spectrum of ABT-199 monohydrochloride Form C of Example 31 of the present invention.

Its X-ray powder diffraction pattern is shown in FIG. 7.
Its TGA pattern is shown in FIG. 8.
Its IR spectrum is shown in FIG. 9.

Example 32

In 100 mg ABT-199 hydrochloride prepared in Preparation Example 2 was added 1 mL butanone to form a suspension, and the mixture was stirred at room temperature for 7 days, and then was filtered under reduced pressure, and the solids were dried at 10° C. for 24 hours under vacuum to obtain 92 mg ABT-199 monohydrochloride Form C.

Example 33

In 100 mg ABT-199 hydrochloride prepared in Preparation Example 2 was added 2 mL water-saturated n-heptane to form a suspension, and the mixture was stirred at 10° C. for 5 days, and then was filtered under reduced pressure, and the solids were dried at 30° C. for 16 hours under vacuum to obtain 78 mg ABT-199 monohydrochloride Form C.

Example 34

In 100 mg ABT-199 hydrochloride prepared in Preparation Example 2 was added 0.4 mL water-saturated ethyl acetate to form a suspension, and the mixture was stirred at 60° C. for 1 day, and then was filtered under reduced pressure, and the solids were dried at 60° C. for 48 hours under vacuum to obtain 18 mg ABT-199 monohydrochloride Form C.

Example 35

In 20 mg ABT-199 hydrochloride prepared in Example 2 was added 2 mL dichloromethane to form a suspension, and the mixture was stirred at 40° C. for 7 days, and was then filtered under reduced pressure, and the solids were dried at 40° C. for 10 hours under vacuum to obtain 15 mg ABT-199 monohydrochloride Form C.

Example 36

In 20 mg ABT-199 hydrochloride prepared in Preparation Example 2 was added 0.5 mL acetone to form a suspension, and the mixture was stirred at 60° C. for 1 day, and was then filtered under reduced pressure, and the solids were dried at 50° C. for 36 hours under vacuum to obtain 17 mg ABT-199 monohydrochloride Form C.

The samples prepared in Examples 32-36 had the same or similar XRPD patterns, TAG patterns and IR spectra (not shown) as those of Example 31, indicating that the samples of Examples 32-36 had the same crystalline form as the sample of Example 31.

Example 37

In 40 mg (0.046 mmol) ABT-199 free base prepared in Preparation Example 1 was added 1.0 mL isopropanol to form a suspension. 9.1 mg (0.092 mmol) 37% concentrated hydrochloric acid was diluted with 0.5 mL isopropanol. While stirring, the hydrochloric acid in isopropanol was added dropwisely to ABT-199 free base, and the reaction system was stirred at room temperature for 3 days, was then filtered under reduced pressure, and dried under vacuum at 30° C. for 24 hours to obtain 41 mg ABT-199 dihydrochloride Form 1.

Figure 10:
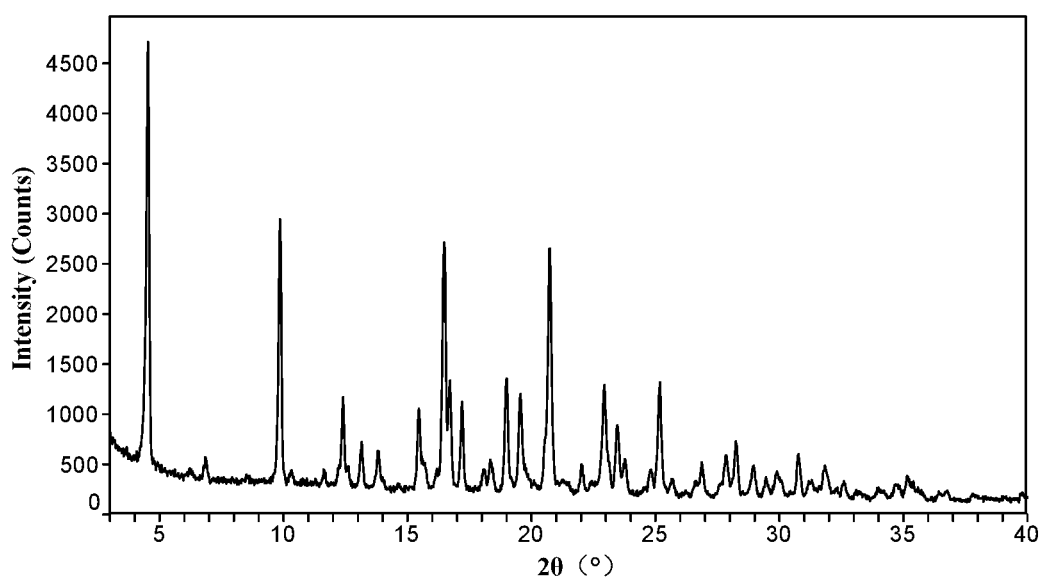
FIG. 10 is an X-ray powder diffraction pattern of ABT-199 dihydrochloride Form 1 of Example 37 of the present invention.
Figure 11:
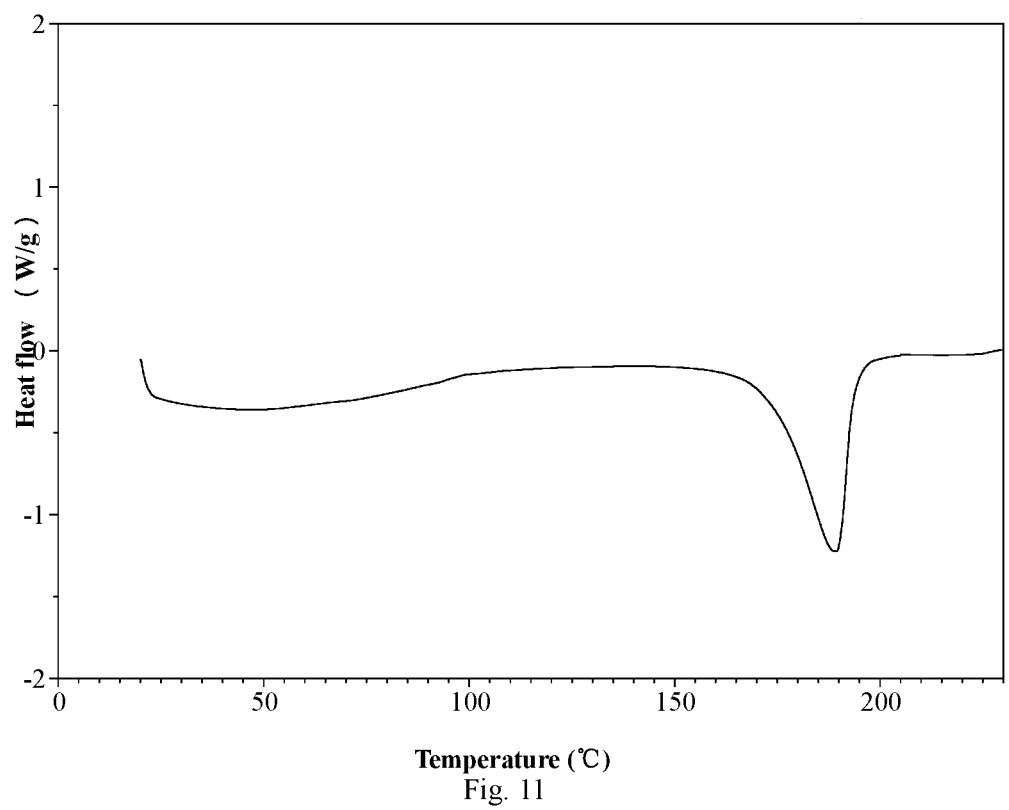
FIG. 11 is a DSC pattern of ABT-199 dihydrochloride Form 1 of Example 37 of the present invention.
Figure 12:
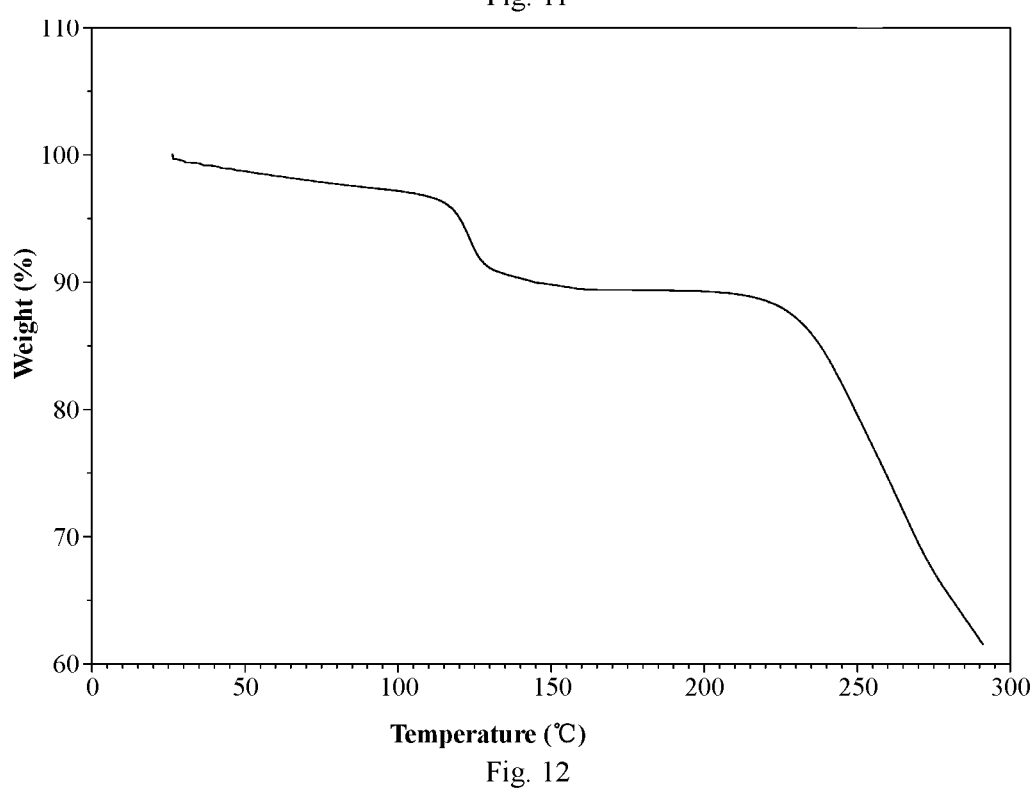
FIG. 12 is a TGA pattern of ABT-199 dihydrochloride Form 1 of Example 37 of the present invention.
Figure 13:
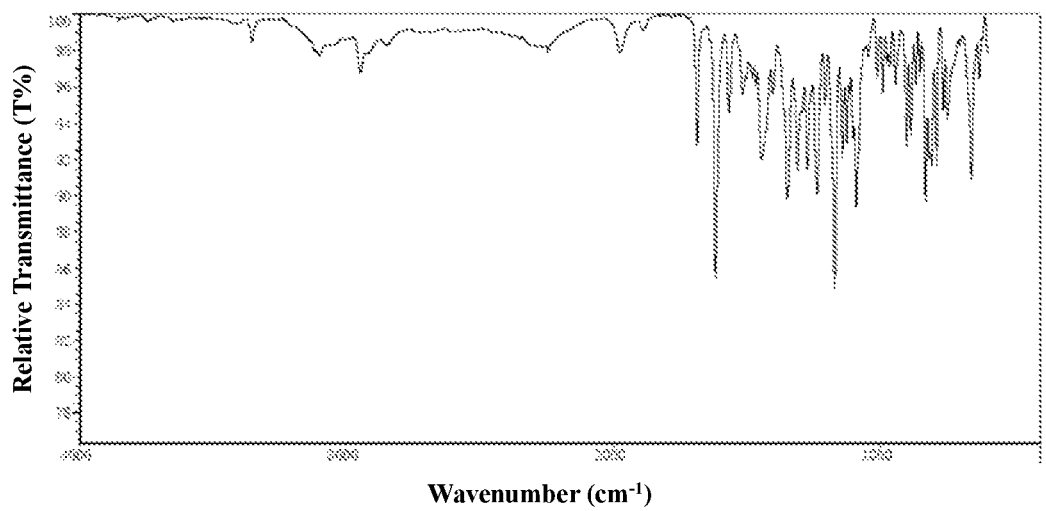
FIG. 13 is an IR spectrum of ABT-199 dihydrochloride Form 1 of Example 37 of the present invention.

Its X-ray powder diffraction pattern is shown in FIG. 10.
Its DSC pattern is shown in FIG. 11.
Its TGA pattern is shown in FIG. 12.
Its IR spectrum is shown in FIG. 13.

Example 38

In 40 mg (0.046 mmol) ABT-199 free base prepared in Preparation Example 1 was added 0.8 mL ethanol to form a suspension, and 23.6 mg (0.097 mmol) 15% concentrated hydrochloric acid was diluted with 0.5 mL ethanol. While stirring, the hydrochloric acid in ethanol was dropwisely added to ABT-199 free base, and the reaction system was stirred at 40° C. for 5 days, was then filtered under reduced pressure, and dried under vacuum at 40° C. for 10 hours to obtain 36 mg ABT-199 dihydrochloride Form 1.

Example 39

In 50 mg (0.058 mmol) ABT-199 free base prepared in Preparation Example 1 was added 0.5 mL acetone to form a suspension, and 26.3 mg (0.144 mmol) 20% concentrated hydrochloric acid was diluted with 0.5 mL acetone. While stirring, hydrochloric acid in acetone was added dropwisely to ABT-199 free base, and the reaction system was stirred at 50° C. for 1 day, was then filtered under reduced pressure, and dried under vacuum at 60° C. for 48 hours to obtain 47 mg ABT-199 dihydrochloride Form 1.

Example 40

In 40 mg (0.046 mmol) ABT-199 free base prepared in Preparation Example 1 was added 0.5 mL acetonitrile to form a suspension, and 15.2 mg (0.104 mmol) 25% concentrated hydrochloric acid was diluted with 0.5 mL acetonitrile. While stirring, hydrochloric acid in acetionitrile was added dropwisely to ABT-199 free base, and the reaction system was stirred at room temperature for 4 days, was then filtered under reduced pressure, and was dried under vacuum at 30° C. for 18 hours to obtain 40 mg ABT-199 dihydrochloride Form 1.

Example 41

In 40 mg (0.046 mmol) ABT-199 free base prepared in Preparation Example 1 was added 0.6 mL methanol to form a suspension, and 14.0 mg (0.115 mmol) 30% concentrated hydrochloric acid was diluted with 0.5 mL methanol. While stirring, the hydrochloric acid in methanol was added dropwisely to ABT-199 free base, and the reaction system was stirred at 60° C. for 2 days, was then filtered under reduced pressure, and was dried under vacuum at 50° C. for 30 hours to obtain 30 mg ABT-199 dihydrochloride Form 1.

Example 42

In 40 mg (0.046 mmol) ABT-199 free base prepared in Preparation Example 1 was added 0.5 mL butanone to form a suspension, and 10.3 mg (0.127 mmol) 37% concentrated hydrochloric acid was diluted with 0.5 mL butanone. While stirring, the hydrochloric acid in butanone was added dropwisely to ABT-199 free base, and the reaction system was stirred at room temperature for 4 days, was then filtered under reduced pressure, and was dried under vacuum at 40° C. for 24 hours to obtain 35 mg ABT-199 dihydrochloride Form 1.

The samples prepared in Examples 38-42 had the same or similar XRPD patterns, TAG patterns and IR spectra (not shown) as those of the sample of Example 37, indicating that the samples of Examples 38-42 had the same crystalline form as the sample of Example 37.

Example 43

In 20 mg ABT-199 hydrochloride prepared in Preparation Example 2 were added 0.2 mL 1,4-dioxane and 0.8 mL water to form a suspension. The suspension was stirred at 60° C. for 3 days, and centrifuged, and the solids were dried at 40° C. for 24 hours under vacuum to obtain 19.75 mg ABT-199 monohydrochloride Form D.

Figure 14:
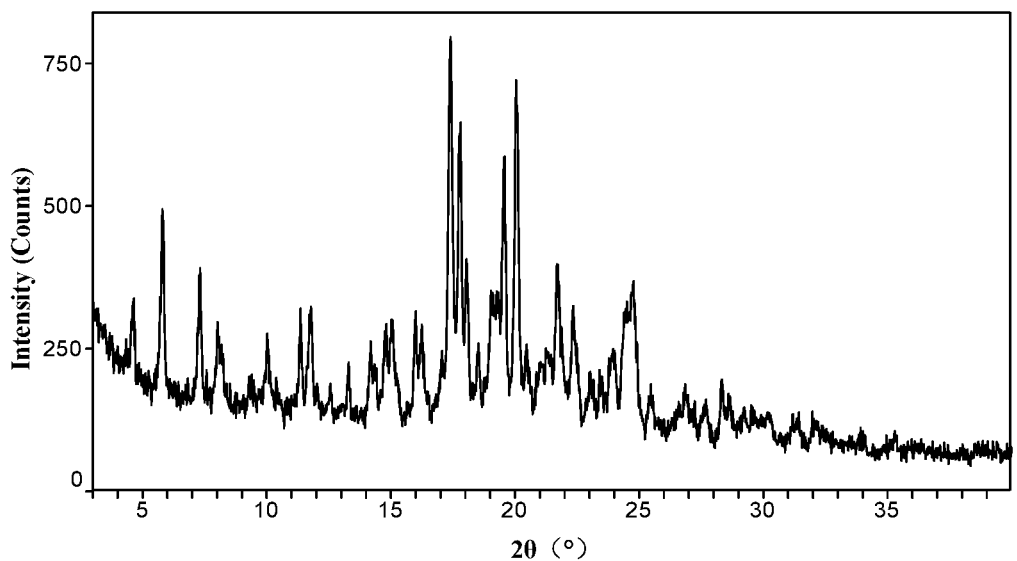
FIG. 14 is an X-ray powder diffraction pattern of ABT-199 monohydrochloride Form D of Example 43 of the present invention

Its X-ray powder diffraction pattern is shown in FIG. 14.

Example 44

In 20 mg ABT-199 hydrochloride prepared in Preparation Example 2 were added 0.4 mL toluene and 0.6 mL n-heptane to form a suspension, and the suspension was stirred at 60° C. for 3 days and then centrifuged, and the solids were dried at 40° C. for 24 hours under vacuum to obtain 18.73 mg ABT-199 monohydrochloride Form E.

Figure 15:
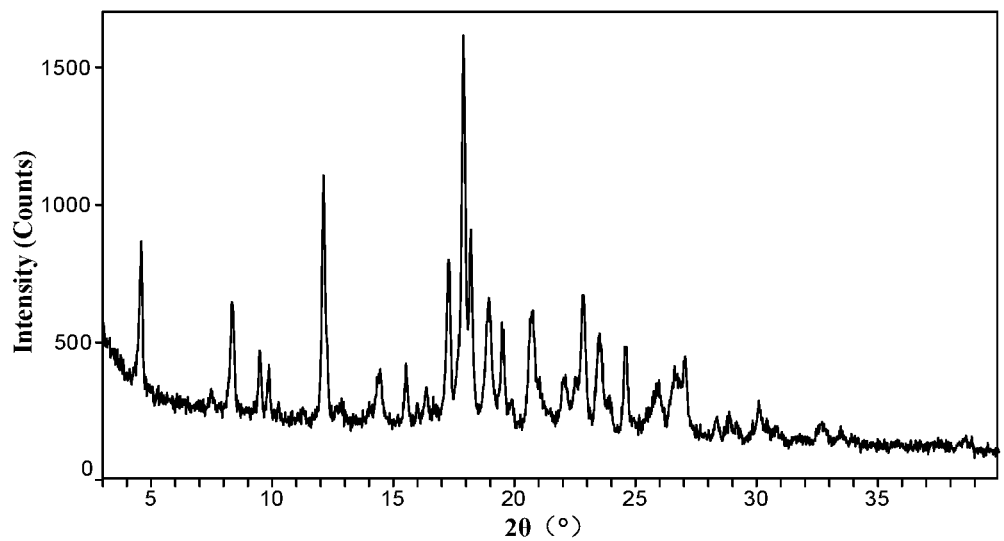
FIG. 15 is an X-ray powder diffraction pattern of ABT-199 monohydrochloride Form E of Example 44 of the present invention

Its X-ray powder diffraction pattern is shown in FIG. 15.

Example 45

In 20 mg ABT-199 hydrochloride prepared in Preparation Example 2 were added 0.2 mL methanol and 0.2 mL chloroform to form a suspension, and the suspension was stirred at 60° C. for 3 days and then centrifuged and dried at 40° C. for 24 hours under vacuum to obtain 18.68 mg ABT-199 monohydrochloride Form F.

Figure 16:
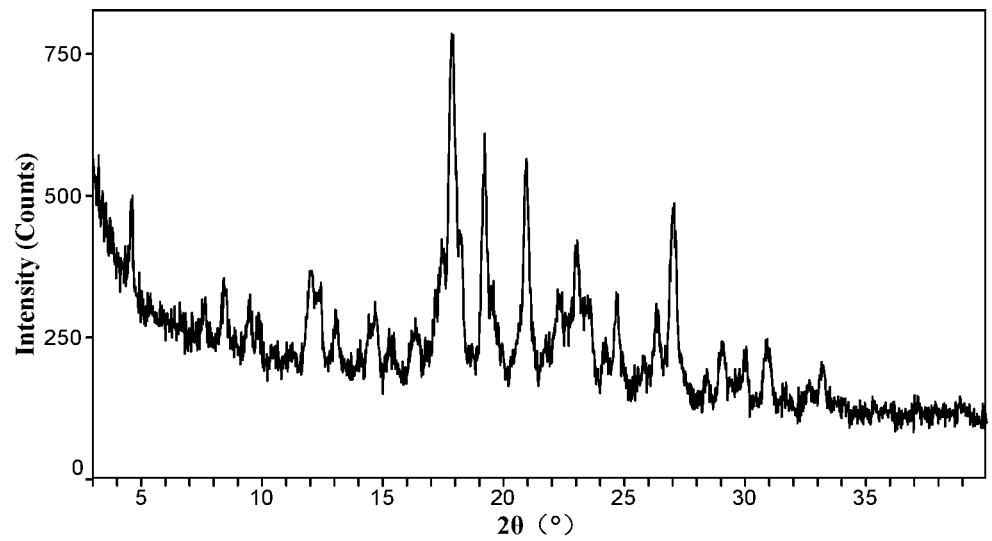
FIG. 16 is an X-ray powder diffraction pattern of ABT-199 monohydrochloride Form F of Example 45 of the present invention

Its X-ray powder diffraction pattern is shown in FIG. 16.

Example 46

In 20 mg ABT-199 hydrochloride prepared in Preparation Example 2 were added 0.2 mL isopropanol, 0.2 mL tetrahydrofuran and 0.2 mL n-heptane to form a suspension, and the suspension was stirred at room temperature for 3 days and then centrifuged, and the solids were dried at 40° C. for 16 hours under vacuum to obtain 19.73 mg ABT-199 monohydrochloride Form G.

Figure 17:
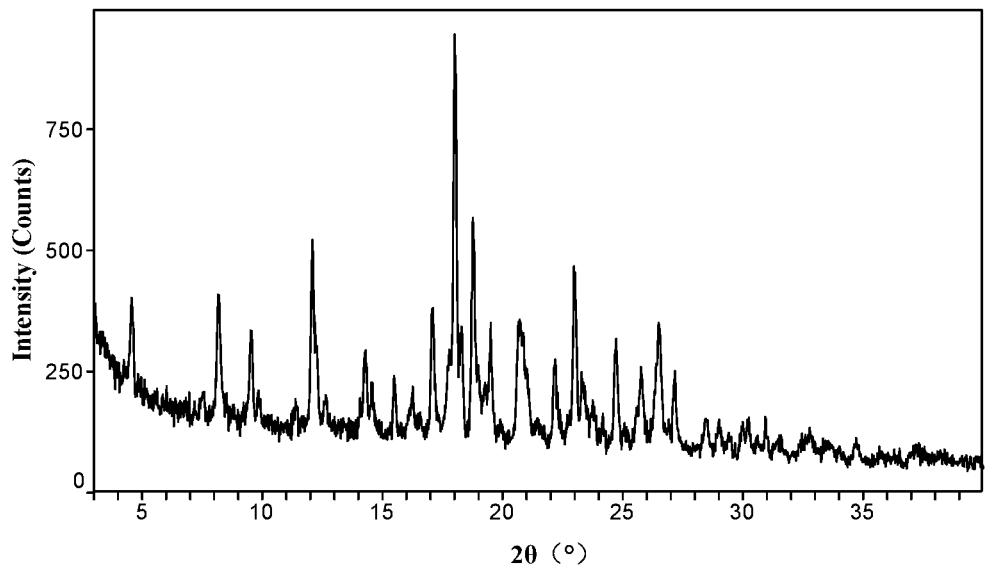
FIG. 17 is an X-ray powder diffraction pattern of ABT-199 monohydrochloride Form G of Example 46 of the present invention

Its X-ray powder diffraction pattern is shown in FIG. 17.

Example 47

In 20 mg ABT-199 hydrochloride prepared in Preparation Example 2 were added 0.2 mL n-propanol, 0.2 mL tetrahydrofuran and 0.2 mL n-heptane to form a suspension. The suspension was stirred at room temperature for 3 days and then centrifuged, and the obtained solids were dried at 40° C. for 16 hours under vacuum to obtain 19.73 mg ABT-199 monohydrochloride Form H.

Figure 18:
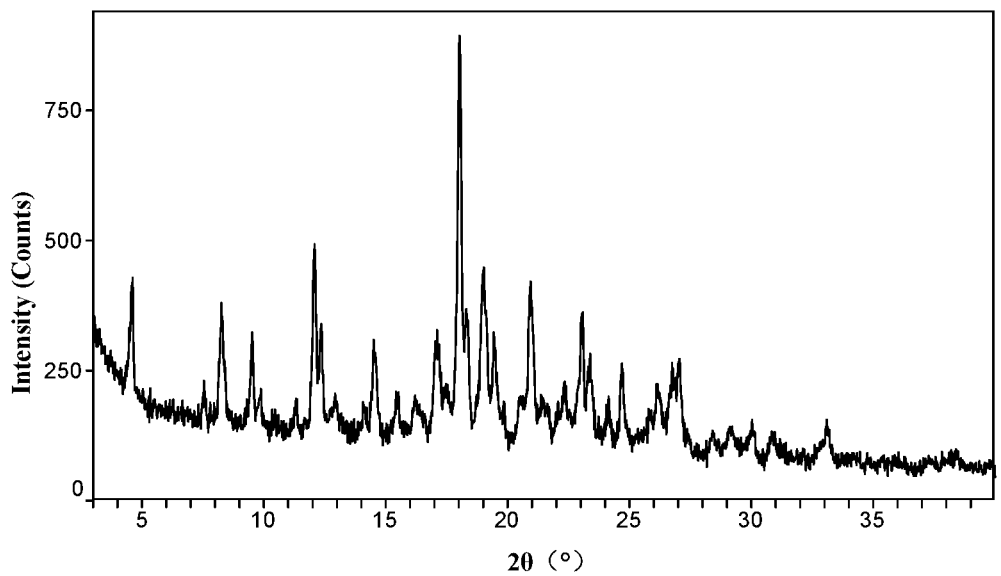
FIG. 18 is an X-ray powder diffraction pattern of ABT-199 monohydrochloride Form H of Example 47 of the present invention
Figure 19:
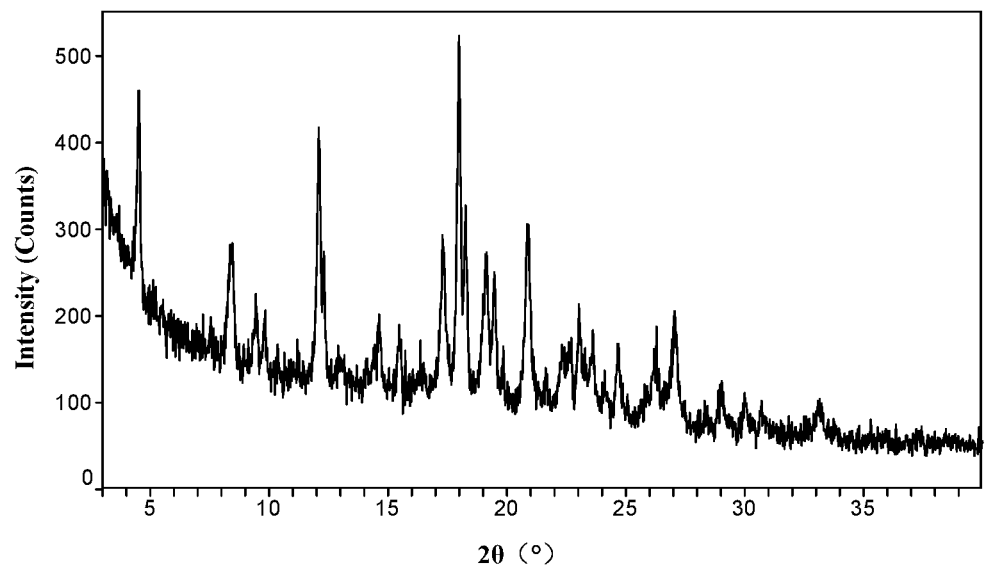
FIG. 19 is an X-ray powder diffraction pattern of ABT-199 monohydrochloride Form I of Example 48 of the present invention

Its X-ray powder diffraction pattern is shown in FIG. 18.

Example 48

In 20 mg ABT-199 hydrochloride prepared in Preparation Example 2 were added 0.2 mL sec-butanol, 0.2 mL tetrahydrofuran and 0.2 mL n-heptane to form a suspension. The suspension was stirred at room temperature for 3 days and then centrifuged, and the obtained solids were dried at 40° C. for 16 hours under vacuum to obtain 20.01 mg ABT-199 monohydrochloride Form I.

Its X-ray powder diffraction pattern is shown in FIG. 18.

Example 49

In 20 mg ABT-199 hydrochloride prepared in Preparation Example 2 were added 0.2 mL n-butanol, 0.2 mL tetrahydrofuran and 0.2 mL n-heptane to form a suspension. The suspension was stirred at room temperature for 3 days and then centrifuged, and the obtained solids were dried at 40° C. for 16 hours under vacuum to obtain 20.01 mg ABT-199 monohydrochloride Form J.

Figure 20:
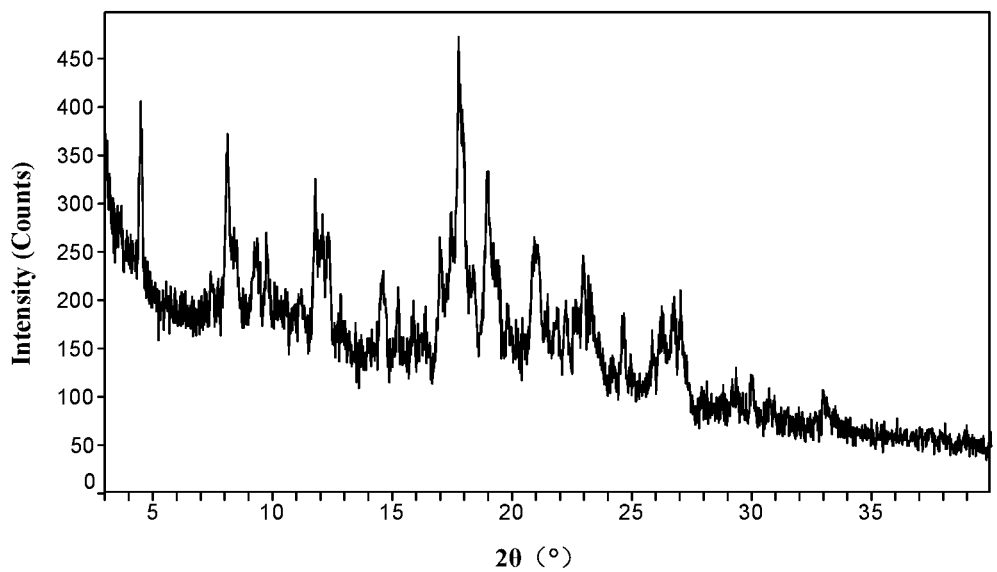
FIG. 20 is an X-ray powder diffraction pattern of ABT-199 monohydrochloride Form J of Example 49 of the present invention

Its X-ray powder diffraction pattern is shown in FIG. 20.

Example 50

In 20 mg ABT-199 hydrochloride prepared in Preparation Example 2 were added 0.2 mL acetone and 0.8 mL water to form a suspension. The suspension was stirred at 50° C. for 3 days and then centrifuged, and the obtained solids were dried at 40° C. for 16 hours under vacuum to obtain 18.73 mg ABT-199 monohydrochloride Form K.

Figure 21:
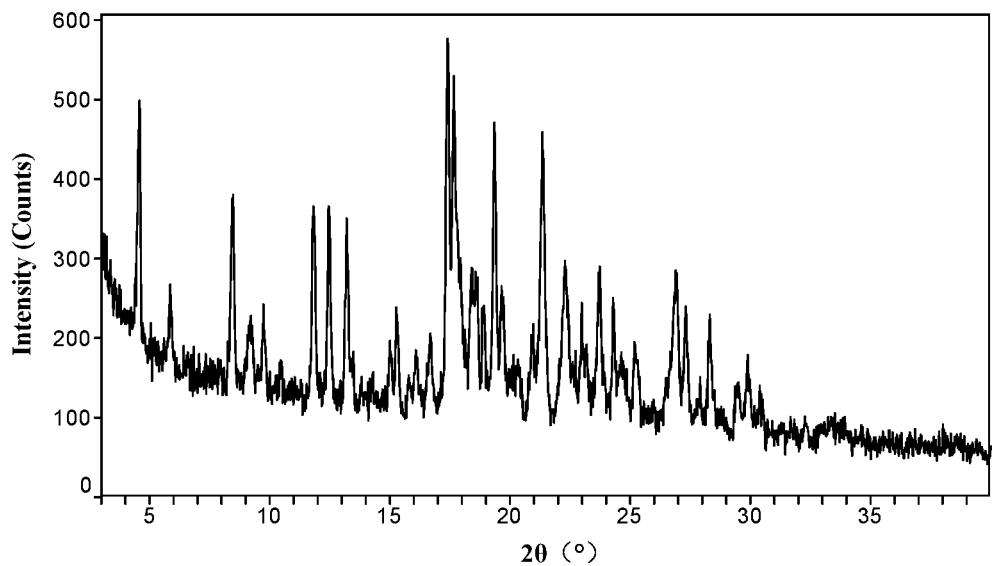
FIG. 21 is an X-ray powder diffraction pattern of ABT-199 monohydrochloride Form K of Example 50 of the present invention

Its X-ray powder diffraction pattern is shown in FIG. 21.

Example 51

In 100 mg ABT-199 hydrochloride prepared in Preparation Example 2 were added 3 mL 1,4-dioxane and 3 mL n-heptane to form a suspension. The suspension was stirred at room temperature for 3 days and then centrifuged, and the obtained solids were dried at 40° C. for 16 hours under vacuum to obtain 97.67 mg ABT-199 monohydrochloride Form L.

Figure 22:
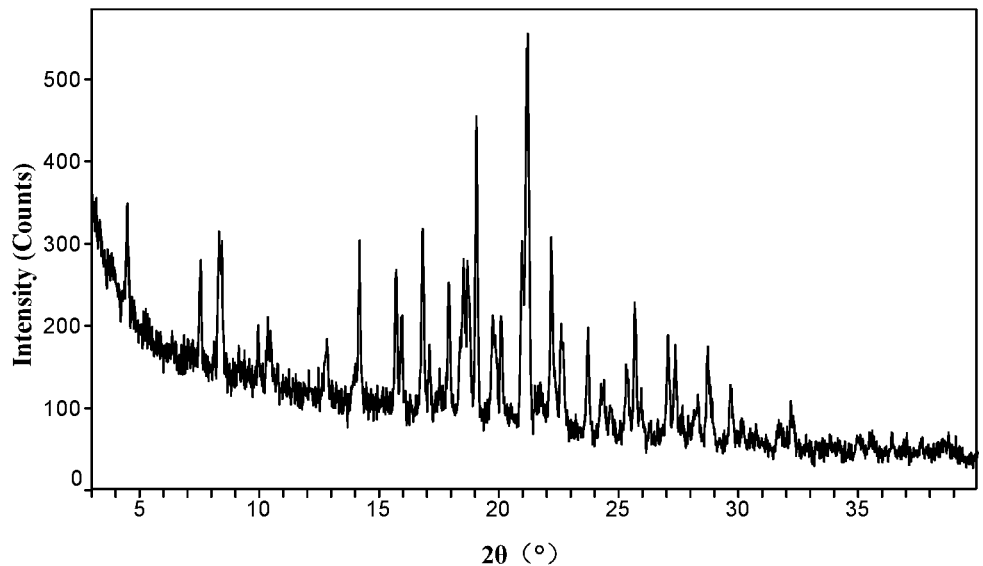
FIG. 22 is an X-ray powder diffraction pattern of ABT-199 monohydrochloride Form L of Example 51 of the present invention

Its X-ray powder diffraction pattern is shown in FIG. 22.

Example 52

In 20 mg ABT-199 hydrochloride prepared in Preparation Example 2 were added 0.2 mL water, 0.2 mL tetrahydrofuran and 0.2 mL n-heptane to form a suspension, and the suspension was stirred at room temperature for 3 days, and then centrifuged, and the solids were dried at 40° C. for 16 hours under vacuum to obtain 19.65 mg ABT-199 monohydrochloride Form M.

Figure 23:
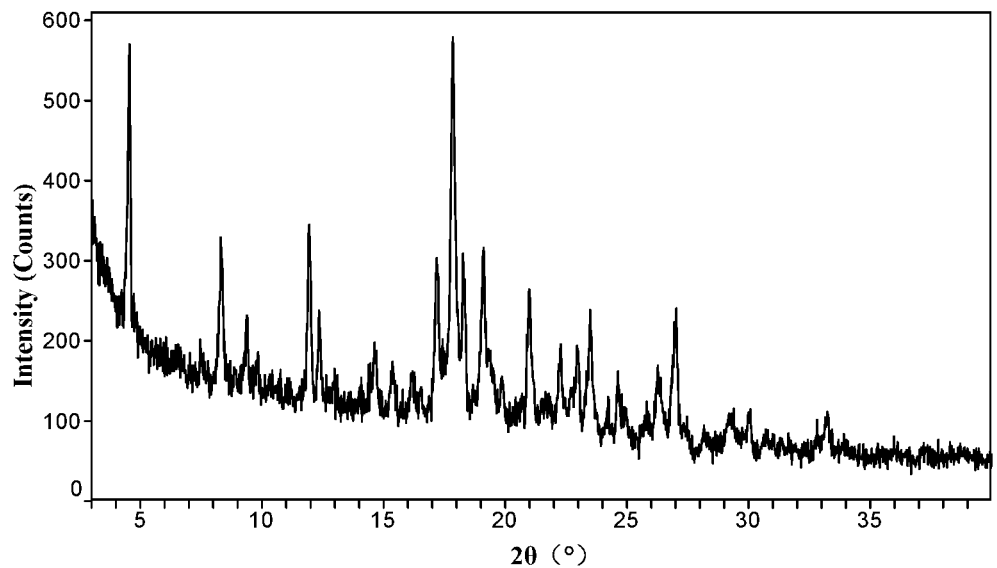
FIG. 23 is an X-ray powder diffraction pattern of ABT-199 monohydrochloride Form M of Example 52 of the present invention

Its X-ray powder diffraction pattern is shown in FIG. 23.

Example 53

In 20 mg ABT-199 hydrochloride prepared in Preparation Example 2 were added 0.6 mL methanol and 0.6 mL water to form a suspension, and the suspension was stirred at 60° C. for 3 days, and then centrifuged, and the solids were dried at 40° C. for 16 hours under vacuum to obtain 19.05 mg ABT-199 monohydrochloride Form N.

Figure 24:
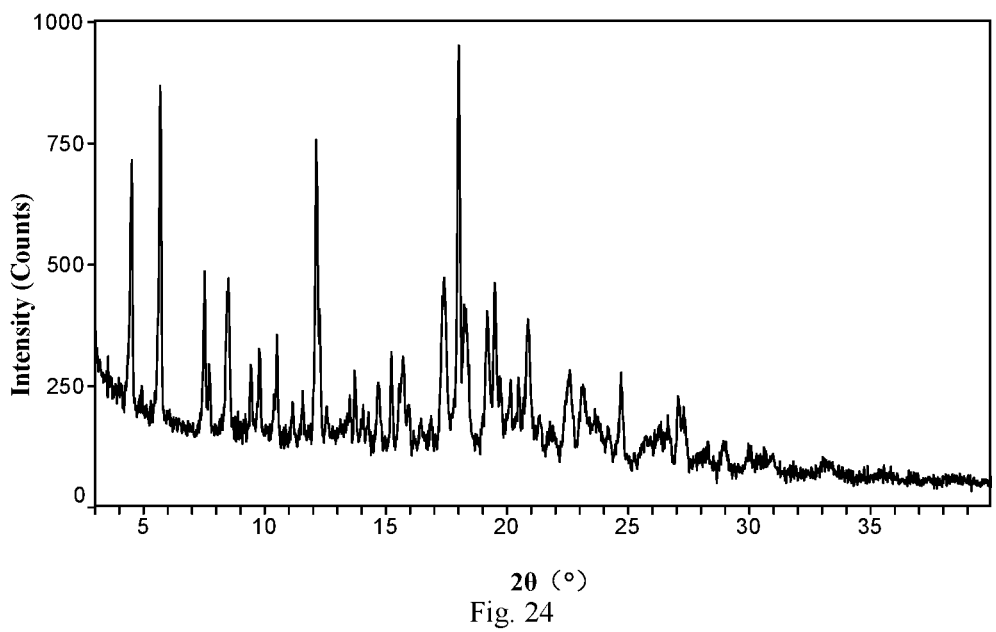
FIG. 24 is an X-ray powder diffraction pattern of ABT-199 monohydrochloride Form N of Example 53 of the present invention

Its X-ray powder diffraction pattern is shown in FIG. 24.

Example 54

As a specific embodiment of oral pharmaceutical compositions, a 300 mg tablet was composed of 330 mg the active ingredient ABT-199 hydrochloride Form A, 152 mg compressible starch, 10 mg cross-linked povidone, 150 mg microcrystalline cellulose and 10 mg silicon dioxide.

Such tablets was prepared by mixing the active ingredients, compressible starch, microcrystalline cellulose and crosslinked povidone, mixing the mixture with silica, and pressing the mixture into tablets.

Example 55-68

The ABT-199 monohydrochloride Form A of Example 54 was replaced with ABT-199 monohydrochloride Form B, Form C, Form D, Form E, Form F, Form G, Form H, Form I, Form J, Form K, Form L, Form M, Form N and ABT-199 dihydrochloride Form 1, respectively, to prepare tablets. The molar amount of the free base in the various salt forms was the same with that of the free base in ABT-199 monohydrochloride Form A, and the fillers and preparation steps were the same as those described in the Example 54.

Example 69

As a specific embodiment of oral pharmaceutical compositions, a 30 mg capsule consisted of 33 mg active ingredient ABT-199 monohydrochloride Form A, 50 mg ethyl cellulose, 15 mg hydroxypropyl methyl cellulose, 70 mg lactose, 30 mg microcrystalline cellulose, 10 mg magnesium stearate and 5 mg talc powder.

Such capsules were prepared by mixing the active ingredients, ethyl cellulose, hydroxypropyl methyl cellulose, lactose and microcrystalline cellulose, granulating the mixture with 75% ethanol, drying the granules, crushing the granules into powder, screening the powder through 80 meshes, then mixing the powder with magnesium stearate and talc powder, and finally filling the mixture into capsules (No. 2 capsule).

Example 70-83

ABT-199 monohydrochloride Form A of Example 69 was replaced by ABT-199 monohydrochloride Form B, Form C, Form D, Form E, Form F, Form G, Form H, Form I, Form J, Form K, Form L, Form M, Form N and ABT-199 dihydrochloride Form 1, respectively, to prepare capsules. The molar amount of free base in various salt forms in the formulation was the same as that of the free base in ABT-199 monohydrochloride Form A, and the fillers and preparation steps were the same as those in the Example 69.

Comparative Example 1

The ABT-199 monohydrochloride Form A prepared in the present invention was compared with the known ABT-199 hydrochloride Form II prepared according to the Preparation Example 2 in a water solubility test. In specific, 10 mg sample was placed in a 50 mL glass bottle, and added with 10 mL deionized water dropwisely at 25° C. to form a suspension. The suspension was treated with ultrasonics until the suspension was stirred for 24 hours and the sample was almost dissolved, the resultant solution was filtered and subject to HPLC detection, and the sample solubility in water was calculated.

TABLE 1

Data for Comparative Experiment 1

| Form | solubility (μg/mL) |
|---|---|
| ABT-199 monohydrochloride Form A of the present invention | About 40 |
| Known ABT-199 hydrochloride Form II | About 20 |

As shown in Table 1, ABT-199 monohydrochloride Form A of the present invention had higher solubility than the known ABT-199 hydrochloride Form II.

Comparative Example 2

The ABT-199 monohydrochloride Form B prepared by the present invention was compared with the known ABT-199 hydrochloride Form II prepared according to the Preparation Example 2. In specific, 30 mg samples were placed at 130° C. for 1 day, and XRPD was carried out to investigate the crystalline stability.

TABLE 2

Data for Comparative Experiment 2

| Sample name | Stored at 130° C. for 1 day |
|---|---|
| ABT-199 monohydrochloride Form B of the present invention | Form B |
| Known ABT-199 monohydrochloride Form II | Phase transition occurred |

Table 2 shows that ABT-199 monohydrochloride Form B of the present invention had better high-temperature-stability than known ABT-199 hydrochloride Form II.

Comparative Example 3

The ABT-199 monohydrochloride Form C prepared by the invention and the known ABT-199 hydrochloride Form II prepared by Preparation Example 2 were used for the competition experiment to test the crystalline form stability. In specific, 20 mg ABT-199 Form II and 20 mg ABT-199 monohydrochloride Form C samples were added to the same water-saturated ethyl acetate to form slurries, which were stirred for 3 days at room temperature or at 40° C., then the samples were analyzed by XRPD to investigate their crystalline form stability.

TABLE 3

Data for Comparative Example 3

| Sample name | Stirring at room temperature for 3 days | Stirring at 40° C. for 3 days |
|---|---|---|
| ABT-199 monohydrochloride Form C of the present invention | Form C | Form C |
| Known ABT-199 monohydrochloride Form II | Convered to Form C | Convered to Form C |

Table 3 shows that through the competitive experiment, Form C remained unchanged after being stirred for 3 days in water-saturated ethyl acetate at room temperature or at 40° C., while Form II changed to Form C after being stirred for 3 days in water-saturated ethyl acetate at room temperature or at 40° C. It shows that ABT-199 monohydrochloride Form C in the present invention was better than the known ABT-199 hydrochloride Form II in water-containing solvents, such as water-saturated ethyl acetate, suggesting its better crystalline stability.

Comparative Example 4

The ABT-199 dihydrochloride Form 1 prepared by the invention and the known ABT-199 hydrochloride Form II prepared according to the Preparation Example 2 were tested for water solubility. In specific, 10 mg sample was placed in a 20 mL glass bottle, and added with 10 mL deionized water at 25° C. to form a suspension, which was stirred for 24 hours at 25° C., filtered, and detected by HPLC, and the solubility of the sample in water was calculated.

TABLE 4

Data for Comparative Example 4

| Form | solubility (μg/mL) |
|---|---|
| ABT-199 dihydrochloride Form 1 of the invention | About 50 |
| Known ABT-199 hydrochloride Form II | About 20 |

Table 4 shows that the ABT-199 dihydrochloride Form 1 of the present invention has higher solubility than the known ABT-199 hydrochloride Form II.

All patents, patent application publications, patent applications and non-patent publications cited in this specification are hereby incorporated by reference in entirety.

The descriptions above are only specific embodiments for illustrating the present invention, which do not limit the present invention. Any changes or alternations, without creative work, made by those skilled in the art within the technical scope as disclosed by the present invention, should fall within the scope of the present invention. The scope of the present invention should be defined by the claims.

We claim:

1. A crystalline form of ABT-199 salt, represented by the following formula (I), (II), (III) or (IV):

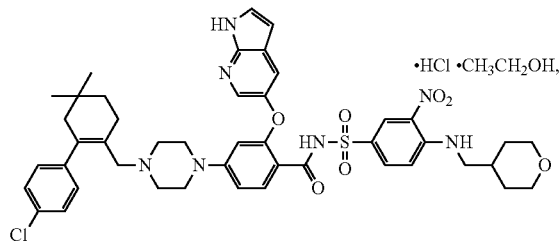

(I)

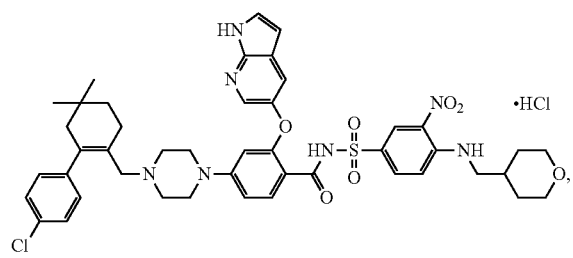

(II)

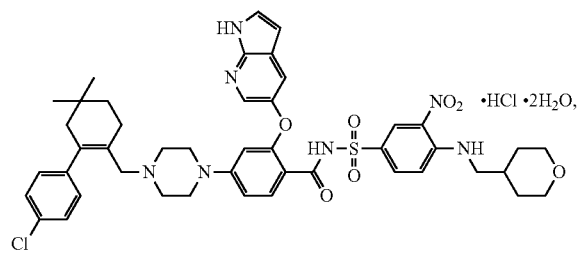

(III)

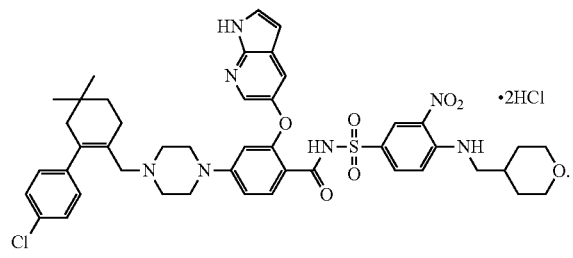

(IV)

2. The crystalline form of claim 1, represented by formula (I) and characterized by an X-ray powder diffraction pattern having characteristic peaks at 4.5±0.2°, 8.3±0.2°, 12.1±0.2°, 17.2±0.2°, 18.0±0.2° and 19.0±0.2° in 2θ.

3. The crystalline form of claim 2, wherein the X-ray powder diffraction pattern has characteristic peaks at 4.5±0.2°, 8.3±0.2°, 9.4±0.2°, 12.1±0.2°, 17.2±0.2°, 18.0±0.2°, 19.0±0.2°, 19.5±0.2°, 20.8±0.2°, 23.0±0.2°, 24.7±0.2° and 27.0±0.2° in 2θ.

4. The crystalline form of claim 2, wherein the X-ray powder diffraction pattern has the following characteristic peaks and relative intensities:

| Diffraction angle 2θ | Relative intensity % |
|---|---|
| 4.5 ± 0.2° | 38.8 |
| 8.3 ± 0.2° | 45.3 |
| 9.4 ± 0.2° | 28.8 |
| 9.8 ± 0.2° | 17.4 |
| 12.1 ± 0.2° | 66.1 |
| 14.5 ± 0.2° | 19.2 |

-continued

| Diffraction angle 2θ | Relative intensity % |
|---|---|
| 17.2 ± 0.2° | 36.0 |
| 18.0 ± 0.2° | 100.0 |
| 19.0 ± 0.2° | 43.3 |
| 19.5 ± 0.2° | 24.7 |
| 20.8 ± 0.2° | 32.0 |
| 23.0 ± 0.2° | 41.4 |
| 23.5 ± 0.2° | 13.7 |
| 24.7 ± 0.2° | 22.3 |
| 26.2 ± 0.2° | 13.3 |
| 27.0 ± 0.2° | 29.5. |

5. The crystalline form of claim 2, wherein the Fourier transform infrared spectrum of the crystalline form has characteristic peaks at wave numbers of 1669, 1522, 1431, 1418, 1269, 1173, 1105, 985, 756 and 660 cm$^{-1}$.

6. The crystalline form of claim 1, represented by formula (II) and characterized by an X-ray powder diffraction pattern having characteristic peaks at 4.6±0.2°, 9.9±0.2°, 12.2±0.2°, 13.3±0.2°, 18.0±0.2° and 20.8±0.2° in 2θ.

7. The crystalline form of claim 6, wherein the X-ray powder diffraction pattern has characteristic peaks at 4.6±0.2°, 7.2±0.2°, 9.1±0.2°, 9.9±0.2°, 12.2±0.2°, 13.3±0.2°, 18.0±0.2°, 18.8±0.2°, 19.1±0.2°, 20.8±0.2°, 22.0±0.2° and 27.0±0.2° in 2θ.

8. The crystalline form of claim 6, wherein the X-ray powder diffraction pattern has the following characteristic peaks and relative intensities:

| Diffraction angel 2θ | Relative intensity % |
|---|---|
| 4.6±0.2° | 23.6 |
| 7.2±0.2° | 20.1 |
| 9.1±0.2° | 20.5 |
| 9.9±0.2° | 31.1 |
| 11.7±0.2° | 15.3 |
| 12.2±0.2° | 25.1 |
| 13.3±0.2° | 100.0 |
| 14.4±0.2° | 21.9 |
| 16.8±0.2° | 17.1 |
| 18.0±0.2° | 29.0 |
| 18.8±0.2° | 36.4 |
| 19.1±0.2° | 37.3 |
| 20.8±0.2° | 32.9 |
| 21.6±0.2° | 17.7 |
| 22.0±0.2° | 33.4 |
| 24.2±0.2° | 23.3 |
| 27.0±0.2° | 35.9. |

9. The crystalline form of claim 6, wherein the Fourier transform infrared spectrum of the crystalline form has characteristic peaks at wave numbers of 1669, 1573, 1431, 1367, 1229, 1205, 1143, 985, 866 and 811 cm$^{-1}$.

10. The crystalline form of claim 6, wherein the crystalline form has the following single crystal structure information:

| Crystal system | Triclinic system |
|---|---|
| Space groups | P$_T$ |
| a (Å) | 12.5124 |
| b (Å) | 13.1206 |
| c (Å) | 15.3840 |
| α (°) | 93.159 |
| β (°) | 96.314 |
| γ (°) | 113.909 |
| Z | 2. |

11. The crystalline form of claim 1, represented by formula (III) and characterized by an X-ray powder diffraction pattern having characteristic peaks at 4.6±0.2°, 8.3±0.2°, 11.9±0.2°, 17.2±0.2° and 17.8±0.2° in 2θ.

12. The crystalline form of claim 11, wherein the X-ray powder diffraction pattern has characteristic peaks at 4.6±0.2°, 8.3±0.2°, 11.9±0.2°, 17.2±0.2°, 17.8±0.2°, 18.5±0.2°, 19.3±0.2°, 21.2±0.2°, 23.6±0.2° and 27.0±0.2° in 2θ.

13. The crystalline form of claim 11, wherein the X-ray powder diffraction pattern has the following characteristic peaks and relative intensities:

| Diffraction angel 2θ | Relative intensity % |
|---|---|
| 4.6 ± 0.2° | 56.6 |
| 8.3 ± 0.2° | 59.4 |
| 9.8 ± 0.2° | 19.1 |
| 11.9 ± 0.2° | 72.3 |
| 12.4 ± 0.2° | 25.0 |
| 15.3 ± 0.2° | 20.7 |
| 17.2 ± 0.2° | 58.2 |
| 17.8 ± 0.2° | 100.0 |
| 18.5 ± 0.2° | 35.5 |
| 19.3 ± 0.2° | 35.5 |
| 21.2 ± 0.2° | 39.3 |
| 22.3 ± 0.2° | 39.3 |
| 23.1 ± 0.2° | 17.0 |
| 23.6 ± 0.2° | 41.6 |
| 24.6 ± 0.2° | 22.5 |
| 27.0 ± 0.2° | 51.4. |

14. The crystalline form of claim 11, wherein the Fourier transform infrared spectrum of the crystalline form has characteristic peaks at wave numbers of 1669, 1605, 1522, 1418, 1367, 1346, 1250, 1173, 904 and 842 $cm^{-1}$.

15. The crystalline form of claim 1, represented by formula (IV) and characterized by an X-ray powder diffraction pattern having characteristic peaks at 4.5±0.2°, 9.9±0.2°, 12.4±0.2°, 16.5±0.2°, 19.0±0.2° and 20.7±0.2° in 2θ.

16. The crystalline form of claim 15, wherein the X-ray powder diffraction pattern has characteristic peaks at 4.5±0.2°, 9.9±0.2°, 12.4±0.2°, 15.5±0.2°, 16.5±0.2°, 16.7±0.2°, 17.2±0.2°, 19.0±0.2°, 19.6±0.2°, 20.7±0.2°, 22.9±0.2° and 25.2±0.2° in 2θ.

17. The crystalline form of claim 15, wherein the X-ray powder diffraction pattern has the following characteristic peaks and relative intensities:

| Diffraction angel 2θ | Relative intensity % |
|---|---|
| 4.5 ± 0.2° | 100.0 |
| 9.9 ± 0.2° | 62.5 |
| 12.4 ± 0.2° | 20.8 |
| 13.2 ± 0.2° | 10.4 |
| 15.5 ± 0.2° | 19.0 |
| 16.5 ± 0.2° | 58.3 |
| 16.7 ± 0.2° | 25.5 |
| 17.2 ± 0.2° | 19.7 |
| 19.0 ± 0.2° | 26.2 |
| 19.6 ± 0.2° | 22.5 |
| 20.7 ± 0.2° | 57.1 |
| 22.9 ± 0.2° | 25.0 |
| 23.5 ± 0.2° | 14.4 |
| 25.2 ± 0.2° | 26.6 |
| 28.2 ± 0.2° | 12.9. |

18. The crystalline form of claim 15, wherein the Fourier transform infrared spectrum of the crystalline form has characteristic peaks at wave numbers of 1687, 1618, 1569, 1447, 1351, 1312, 1275, 1238, 1172, 1091, 831, 790 and 659 $cm^{-1}$.

19. A pharmaceutical composition comprising a therapeutically or preventively effective amount of the crystalline form according to claim 1, and at least one pharmaceutically acceptable carrier.

20. A method for preparing the crystalline form according to claim 1, comprising:

(a)
forming a suspension of ABT-199 monohydrochloride solid in ethanol or in a mixed solvent of ethanol and another organic solvent, wherein the another solvent comprises water, alkane, $C_4$ to $C_5$ ester, $C_4$ to $C_6$ ether, acetonitrile, tetrahydrofuran or a mixture thereof, stirring the suspension for crystallization, and separating and drying precipitated crystals to obtain the crystalline form represented by formula (I);

or (b)
heating ABT-199 monohydrochloride Form A or ABT-199 hydrochloride Form II from room temperature to 130° C. at a heating rate of 5 to 20° C./min, holding the sample at that temperature for a holding time comprising 5 to 35 minutes until complete desolvation, and then cooling the sample to room temperature at a cooling rate of 5 to 20° C./min to obtain the crystalline form represented by formula (II);

wherein the ABT-199 monohydrochloride Form A is represented by formula (I) and characterized by an X-ray powder diffraction pattern having characteristic peaks at 4.5±0.2°, 8.3±0.2°, 12.1±0.2°, 17.2±0.2°, 18.0±0.2° and 19.0±0.2° in 2θ;

or (c)
placing a sample ABT-199 monohydrochloride Form A or ABT-199 hydrochloride Form II in an environment at a temperature comprising 130 to 150° C. for a period of time comprising 20 to 40 minutes until the solvent is completely removed to obtain a solvent-removed product, and then placing the solvent-removed product at room temperature to obtain the crystalline form represented by formula (II);

wherein the ABT-199 monohydrochloride Form A is represented by formula (I) and characterized by an X-ray powder diffraction pattern having characteristic peaks at 4.5±0.2°, 8.3±0.2°, 12.1±0.2°, 17.2±0.2°, 18.0±0.2° and 19.0±0.2° in 2θ;

or (d)
forming a suspension of ABT-199 monohydrochloride solid in dichloromethane, methanol, water-saturated ester/alkane, $C_3$ to $C_4$ ketone or a mixture thereof, stirring the suspension for crystallization, separating and drying the precipitated crystals, to obtain the crystalline form represented by formula (III);

or (e)
mixing and stirring ABT-199 free base and hydrochloric acid solution at a molar ratio of 1:2 to 1:2.5 in a solvent, and separating resulting solids to obtain the crystalline form represented by formula (IV);

wherein the solvent comprises $C_1$ to $C_4$ alcohol, $C_3$ to $C_4$ ketone, acetonitrile or a mixture thereof.

21. The method of claim 20:
wherein in (a):
the another organic solvent comprises water, n-heptane, methyl tert-butyl ether, tetrahydrofuran or a mixture thereof; or
the method is carried out at a temperature comprising 10 to 60° C.; or
the method is carried out at room temperature; or
the stirring time comprises from 1 day to 7 days; or
the stirring time comprises 3 days to 7 days; or
the drying temperature comprises from 10° C. to 60° C.; or
the drying temperature comprises 10° C. to 40° C.; or
the drying time comprises from 10 hours to 48 hours; or
the drying time comprises 10 hours to 24 hours; or
the weight to volume ratio of ABT-199 monohydrochloride to the solvent comprises 10 mg/mL to 100 mg/mL; or
the weight to volume ratio of ABT-199 monohydrochloride to the solvent comprises 20 mg/mL to 50 mg/mL;
or wherein in (b):
the holding time comprises 20 to 35 minutes; or
the holding time comprises 20 to 30 minutes; or
the heating rate comprises 5 to 10° C./min; or
the cooling rate is preferably 10 to 20° C./min;
or wherein in (c):
the said environmental temperature comprises 140 to 150° C.; or
the placing of the sample in the environment is for a time comprising 20 to 30 minutes;
or wherein in (d):
the solvent comprises dichloromethane, methanol, water-saturated ethyl acetate, water-saturated n-heptane, methyl ethyl ketone or a mixture thereof; or
the method is carried out at a temperature comprising 10 to 60° C.; or
the method is carried out at room temperature; or
stirring is carried out for a time comprising from 1 to 7 days; or
stirring is carried out for a time comprising from 3 to 7 days; or
drying is carried out at a temperature comprising from 10 to 60° C.; or
drying is carried out at a temperature comprising from 10 to 40° C.; or
drying is carried out for a time comprising 10 to 48 hours; or
drying is carried out for a time comprising from 10 to 24 hours; or
the weight to volume ratio of ABT-199 monohydrochloride to solvent comprises 10 mg/mL to 100 mg/mL; or
the weight to volume ratio of ABT-199 monohydrochloride to solvent comprises 20 mg/mL to 50 mg/mL;
or wherein in (e):
the solvent comprises isopropanol, acetone, acetonitrile or a mixture thereof; or
the method is conducted at a temperature comprising 10 to 50° C.; or
the method is conducted at room temperature; or
stirring is conducted for a time comprising from 1 to 7 days; or
stirring is conducted for a time comprising from 3 to 7 days; or
the drying is conducted at a temperature comprising from 10 to 60° C.; or
the drying is conducted at a temperature comprising from 10 to 40° C.; or
the drying is conducted for a time comprising from 10 to 48 hours; or
the drying is conducted for a time comprising from 10 to 24 hours; or
the weight to volume ratio of ABT-199 free base to solvent comprises 40 mg/mL to 100 mg/mL; or
the weight to volume ratio of ABT-199 free base to solvent comprises 40 mg/mL to 80 mg/mL.

* * * * *